US009642835B2

(12) United States Patent
Wandinger-Ness et al.

(10) Patent No.: US 9,642,835 B2
(45) Date of Patent: May 9, 2017

(54) MODULATORS OF GTPASE AND USE IN RELEVANT TREATMENT

(71) Applicants: STC.UNM, Albuquerque, NM (US); University of Kansas, Lawrence, KS (US)

(72) Inventors: Angela Wandinger-Ness, Albuquerque, NM (US); Larry Sklar, Albuquerque, NM (US); Zurab Surviladze, Albuquerque, NM (US); Tudor Oprea, Albuquerque, NM (US); Laurie Hudson, Albuquerque, NM (US); Jeffrey Aube, Lawrence, KS (US); Jennifer E. Golden, Olathe, KS (US); Chad E. Schroeder, Lawrence, KS (US); Denise S. Simpson, Fairborn, KS (US); Julica J. Noth, Munich (DE)

(73) Assignees: STC.UNM, Albuquerque, NM (US); UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 13/867,658

(22) Filed: Apr. 22, 2013

(65) Prior Publication Data
US 2013/0345277 A1   Dec. 26, 2013

Related U.S. Application Data

(62) Division of application No. 13/161,832, filed on Jun. 16, 2011, now abandoned.

(60) Provisional application No. 61/397,864, filed on Jun. 17, 2010.

(51) Int. Cl.
| *A61K 31/415* | (2006.01) |
| *A61K 45/06* | (2006.01) |
| *C07D 231/06* | (2006.01) |
| *A61K 31/403* | (2006.01) |
| *A61K 31/407* | (2006.01) |

(52) U.S. Cl.
CPC .......... *A61K 31/403* (2013.01); *A61K 31/407* (2013.01); *A61K 31/415* (2013.01); *A61K 45/06* (2013.01); *C07D 231/06* (2013.01)

(58) Field of Classification Search
None
See application file for complete search history.

(56) References Cited

U.S. PATENT DOCUMENTS

| 2003/0100594 A1 | 5/2003 | Masferrer et al. |
| 2003/0220376 A1 | 11/2003 | Masferrer et al. |
| 2007/0066651 A1 | 3/2007 | Cuberes Altisen et al. |

FOREIGN PATENT DOCUMENTS

EP    1787122 B1    10/2010

OTHER PUBLICATIONS

Zins et al., Targeting Cdc42 with the small molecule drug AZA197 suppresses primary colon cancer growth and prolongs survival in a preclinical mouse xenograft model by downregulation of PAK1 activity. Journal of Translational Medicine 2013, 11, 295.*
Hong et al., Characterization of Cdc42 Protein Inhibitors and Its Use as a Molecular Probe. Journal of Biological Chemistry 2013, 288, 8531-8543.*
Zins et al., A Rac1/Cdc42 GTPase-Specific Small Molecule Inhibitor Suppresses Growth of Primary Human Prostate Cancer Xenograft and Prolong Survival in Mice. PLOS ONE 2013, 8, 1-13.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Kim et al., Selective Cyclooxygenase Inhibitors Increase Paclitaxel Sensitivity of Taxane-Resistant Ovarian Cancer Cell Lines via Suppresion of p-glycoprotein Expression; (Abstract #5115). Presented at the AACR annual meeting, Apr. 18-22, Denver, CO.*
Takai, Y., Sasaki, T. & Matozaki, T. Small GTP-binding proteins. Physiol. Rev. 81, 153-208 (2001).
Raftopoulou, M. & Hall, A. Cell migration: Rho GTPases lead the way. Dev. Biol. 265, 23-32 (2004).
Wennerberg, K., Rossman, K.L. & Der, C.J. The Ras superfamily at a glance. J. Cell Sci.118, 843-846 (2005).
Stein, M.P., Dong, J. & Wandinger-Ness, A. Rab proteins and endocytic trafficking:potential targets for therapeutic intervention. Adv. Drug Deliv. Rev. 55, 1421-1437 (2003).
Brumell, J.H. & Scidmore, M.A. Manipulation of rab GTPase function by intracellularbacterial pathogens. Microbiol. Mol. Biol. Rev. 71, 636-652 (2007).

(Continued)

*Primary Examiner* — Matthew Coughlin
*Assistant Examiner* — Po-Chih Chen
(74) *Attorney, Agent, or Firm* — Henry D. Coleman; R. Neil Sudol

(57) ABSTRACT

The present invention relates to molecules which function as selective modulators (i.e., inhibitors and agonists, preferably inhibitors) of the Ras-homologous (Rho) family of small GTPases, in particular, Cdc42 GTPase and their use to treat diseases, for example cancers, including metastatic cancer, where Cdc42 GTPase is overexpressed or hyperactivated, genetic and acquired diseases where activation of Cdc42 GTPase plays a pivotal role (e.g., neurodegenerative diseases), rheumatoid arthritis, atherosclerosis, diabetes type I, autosomal polycystic kidney diease, cystic kidney disease, precystic kidney disease and microbial infections. Additionally, compounds according to the present invention may be used to inhibit rejection (graft host response) in transplant patients (pursuant to transplantation), to promote immunosuppression, anti-inflammatory response and to mobilize stem cell (migration) in patients in need, among others.

35 Claims, 17 Drawing Sheets

(56) References Cited

OTHER PUBLICATIONS

Minutolo, F. et al. Variously substituted (phosphonoacetamido)oxy analogues of geranylgeranyl diphosphate (GGdP) as GGdP-transferase (GGTase) inhibitors and antiproliferative agents. Med. Chem. 1, 239-244 (2005).

Morgillo, F. & Lee, H.Y. Lonafarnib in cancer therapy. Expert Opin. Investig. Drugs 15, 709-719 (2006).

Druker, B.J. et al. Effects of a selective inhibitor of the Abl tyrosine kinase on the growth of Bcr-Abl positive cells. Nat. Med. 2, 561-566 (1996).

Traxler, P. et al. Use of a pharmacophore model for the design of EGF-R tyrosine kinase inhibitors: 4-(phenylamino) pyrazolo[3,4-d]pyrimidines. J. Med. Chem. 40, 3601-3616 (1997).

Ciardiello, F. et al. Antitumor effect and potentiation of cytotoxic drugs activity in human cancer cells by ZD-1839 (Iressa), an epidermal growth factor receptor-selective tyrosine kinase inhibitor. Clin. Cancer Res. 6, 2053-2063 (2000).

Al-Obeidi, F.A. & Lam, K.S. Development of inhibitors for protein tyrosine kinases. Oncogene 19, 5690-5701 (2000).

Buday, L. & Downward, J. Many faces of Ras activation. Biochim. Biophys. Acta 1786:178-187 (2008).

Jaffe, A.B. & Hall, A. Rho GTPases: biochemistry and biology. Annu. Rev. Cell Dev. Biol.21, 247-269 (2005).

Bucci, C. & Chiariello, M. Signal transduction gRABs attention. Cell Signal. 18, 1-8 (2006).

Brown, R., Marshall, C.J., Pennie, S.G. & Hall, A. Mechanism of activation of an N-ras gene in the human fibrosarcoma cell line HT1080. EMBO J. 3, 1321-1326 (1984).

Bar-Sagi, D. & Feramisco, J.R. Microinjection of the ras oncogene protein into PC12 cells induces morphological differentiation. Cell 42, 841-848 (1985).

Braun, B.S. & Shannon, K. Targeting Ras in myeloid leukemias. Clin. Cancer Res. 14, 2249-2252 (2008).

Schwartz, S.L., Cao, C., Pylypenko, O., Rak, A. & Wandinger-Ness, A. Rab GTPases at a glance. J. Cell Sci. 120, 3905-3910 (2007).

Cheng, K.W., Lahad, J.P., Gray, J.W. & Mills, G.B. Emerging role of RAB GTPases in cancer and human disease. Cancer Res 65, 2516-2519 (2005).

Williams, D.A. et al. Dominant negative mutation of the hematopoietic-specific Rho GTPase, Rac2, is associated with a human phagocyte immunodeficiency. Blood 96, 1646-1654 (2000).

Aspenstrom, P., Lindberg, U. & Hall, A. Two GTPases, Cdc42 and Rac, bind directly to a protein implicated in the immunodeficiency disorder Wiskott-Aldrich syndrome. Curr. Biol. 6, 70-75 (1996).

Khosravi-Far, R. et al. Dbl and Vav mediate transformation via mitogen-activated protein kinase pathways that are distinct from those activated by oncogenic Ras. Mol. Cell Biol. 14, 6848-6857 (1994).

Habets, G.G. et al. Identification of an invasion-inducing gene, Tiam-1, that encodes a protein with homology to GDP-GTP exchangers for Rho-like proteins. Cell 77, 537-549 (1994).

Patel, V. et al. Persistent activation of Rac1 in squamous carcinomas of the head and neck: evidence for an EGFR/Vav2 signaling axis involved in cell invasion. Carcinogenesis 28, 1145-1152 (2007).

Ellenbroek, S.I. & Collard, J.G. Rho GTPases: functions and association with cancer. Clin. Exp. Metastasis 24, 657-672 (2007).

Gao, Y., Dickerson, J.B., Guo, F., Zheng, J. & Zheng, Y. Rational design and characterization of a Rac GTPase-specific small molecule inhibitor. Proc. Natl. Acad. Sci. USA 101, 7618-7623 (2004).

Nassar, N., Cancelas, J., Zheng, J., Williams, D.A. & Zheng, Y. Structure-function based design of small molecule inhibitors targeting Rho family GTPases. Curr. Top. Med. Chem. 6, 1109-1116 (2006).

Schwartz, S.L. et al. Flow cytometry for real-time measurement of guanine nucleotide binding and exchange by Ras-like GTPases. Anal. Biochem. 381, 258-266 (2008).

Nolan, J.P. & Sklar, L.A. The emergence of flow cytometry for sensitive, real-time measurements of molecular interactions. Nat. Biotechnol. 16, 633-638 (1998).

Kuckuck, F.W., Edwards, B.S. & Sklar, L.A. High throughput flow cytometry. Cytometry 44, 83-90 (2001).

Young, S.M. et al. High-throughput screening with HyperCyt flow cytometry to detect small molecule formylpeptide receptor ligands. J. Biomol. Screen 10, 374-382 (2005).

Sklar, L.A., Carter, M.B. & Edwards, B.S. Flow cytometry for drug discovery, receptor pharmacology and high-throughput screening. Curr. Opin. Pharmacol. 7, 527-534 (2007).

Simons, P.C. et al. Simultaneous in vitro Molecular Screening of Protein-Peptide Interactions by Flow Cytometry using Six Bcl-2 Family Proteins as Examples. Nature Protocols 6, 943-952 (2008).

Bagrodia, S., Taylor, S.J., Creasy, C.L., Chernoff, J. & Cerione, R.A. Identification of a mouse p21Cdc42/Rac activated kinase. J. Biol. Chem. 270, 22731-22737 (1995).

Lim, L., Manser, E., Leung, T. & Hall, C. Regulation of phosphorylation pathways by p21 GTPases. The p21 Ras-related Rho subfamily and its role in phosphorylation signaling pathways. Eur. J. Biochem. 242, 171-185 (1996).

Thompson, G., Owen, D., Chalk, P.A. & Lowe, P.N. Delineation of the Cdc42/Rac-binding domain of p21-activated kinase. Biochemistry 37, 7885-7891 (1998).

Benard, V. & Bokoch, G.M. Assay of Cdc42, Rac, and Rho GTPase activation by affinity methods. Methods Enzymol. 345, 349-359 (2002).

Ridley, A.J., Paterson, H.F., Johnston, C.L., Diekmann, D. & Hall, A. The small GTPbinding protein rac regulates growth factor-induced membrane ruffling. Cell 70, 401-410 (1992).

Nobes, C.D. & Hall, A. Rho, rac, and cdc42 GTPases regulate the assembly of multimolecular focal complexes associated with actin stress fibers, lamellipodia, and filopodia. Cell 81, 53-62 (1995).

Guillemot, J.C., Montcourrier, P., Vivier, E., Davoust, J. & Chavrier, P. Selective control of membrane ruffling and actin plaque assembly by the Rho GTPases Rac1 and CDC42 in FcepsilonRI-activated rat basophilic leukemia (RBL-2H3) cells. J. Cell Sci. 110, 2215-2225 (1997).

Djouder, N., Prepens, U., Aktories, K. & Cavalie, A. Inhibition of calcium releaseactivated calcium current by Rac/Cdc42-inactivating clostridial cytotoxins in RBL cells. J. Biol. Chem. 275, 18732-18738 (2000).

Itoh, R.E. et al. Activation of rac and cdc42 video imaged by fluorescent resonance energy transfer-based single-molecule probes in the membrane of living cells. Mol. Cell Biol. 22, 6582-6591 (2002).

Shutes, A. et al. Specificity and mechanism of action of EHT 1864, a novel small molecule inhibitor of Rac family small GTPases. J. Biol. Chem. 282, 35666-35678 (2007).

Parsons, J.T. Integrin-mediated signalling: regulation by protein tyrosine kinases and small GTP-binding proteins. Curr. Opin. Cell Biol. 8, 146-152 (1996).

Chigaev, A., Waller, A., Amit, O. & Sklar, L.A. Galphas-coupled receptor signaling actively down-regulates alpha4betal-integrin affinity: a possible mechanism for cell deadhesion. BMC Immunol. 9, 26-41 (2008).

Onesto, C., Shutes, A., Picard, V., Schweighoffer, F. & Der, C.J. Characterization of EHT1864, a novel small molecule inhibitor of Rac family small GTPases. Methods Enzymol. 439, 111-129 (2008).

Gupta, S. et al. Molecular cloning of IBP, a SWAP-70 homologous GEF, which is highly expressed in the immune system. Hum. Immunol. 64, 389-401 (2003).

Price, M.O., Atkinson, S.J., Knaus, U.G. & Dinauer, M.C. Rac activation induces NADPH oxidase activity in transgenic COSphox cells, and the level of superoxide production is exchange factor-dependent. J. Biol. Chem. 277, 19220-19228 (2002).

Denicola, G. & Tuveson, D.A. VAV1: a new target in pancreatic cancer? Cancer Biol.Ther. 4, 509-511 (2005).

Agarwal V, Hammerschmidt S. Cdc42 and the phosphatidylinositol 3-kinase-Akt pathway are essential for PspC-mediated internalization of pneumococci by respiratory epithelial cells. J Biol Chem. 2009;284:19427-36.

Boettner B, Van Aelst L. The role of Rho GTPases in disease development. Gene. 2002; 286:155-74.

(56) References Cited

OTHER PUBLICATIONS

Bos JL, Rehmann H, Wittinghofer A. GEFs and GAPs: critical elements in the control of small G proteins. Cell. 2007;129(5):865-77.
Chang YW, Bean RR, Jakobi R. Targeting RhoA/Rho kinase and p21-activated kinase signaling to prevent cancer development and progression. Recent Pat Anticancer Drug Discov. 2009;4:110-24.
Chimini G, Chavrier P. Function of Rho family proteins in actin dynamics during phagocytosis and engulfment. Nat Cell Biol. 2000; 2: E191-6.
Dutra JM, Bonilha VL, De Souza W, Carvalho TM. Role of small GTPases in Trypanosoma cruzi invasion in MDCK cell lines. Parasitol Res. 2005;96:171-7.
Etienne-Manneville S, Hall A: Rho GTPases in cell biology. Nature 2002; 420:629-635.
Faid-Allah, HM; Mokhtar, HM. Pyrazole derivatives with possible hypoglycemic activity. Indian Journal of Chemistry, Section B: Organic Chemistry Including Medicinal Chemistry 1988; 27B: 245-249.
Gao Y, Dickerson JB, Guo F, Zheng J, Zheng Y. Rational design and characterization of a Rac GTPasespecific small molecule inhibitor. Proc Natl Acad Sci May 18, 2004;101(20):7618-23.
Gómez del Pulgar T, Benitah SA, Valerón PF, Espina C, Lacal JC. Rho GTPase expression in tumorigenesis: evidence for a significant link. Bioessays. 2005;27:602-13.
He B, Chen P, Chen Sy, Vancura KL, Michaelis S, Powers S. RAM2, an essential gene of yeast, and RAM1 encode the two polypeptide components of the farnesyltransferase that prenylates a-factor and Ras proteins. Proc Natl Acad Sci U S A. 1991, 88:11373-7.
Isleyen, A; Dogan, O. Application of ferrocenyl substituted aziridinylmethanols (FAM) as chiral ligands in enantioselective conjugate addition of diethylzinc to enones. Tetrahedron: Asymmetry. 2007:18: 679-684.
Jaffe AB, Hall A: Rho GTPases: biochemistry and biology. Annu Rev Cell Dev Biol 2005; 21:247-269.
Johnson JL, Erickson JW, Cerione RA. New insights into how the Rho guanine nucleotide dissociation inhibitor regulates the interaction of Cdc42 with membranes. J. Biol. Chem. 2009; 284:23860-71.
Kozma R, Ahmed S, Best A, Lim L. The Ras-related protein Cdc42Hs and bradykinin promote formation of peripheral actin microspikes and filopodia in Swiss 3T3 fibroblasts. Mol Cell Biol. 1995;15:1942-52.
Kuckuck FW, Edwards BS, Sklar LA. High throughput flow cytometry. Cytometry. 2001;44:83-90.
Pelish HE, Peterson JR, Salvarezza SB, Rodriguez-Boulan E, Chen JL, Stamnes M, Macia E, Feng Y, Shair MD, Kirchhausen T. Secramine inhibits Cdc42-dependent functions in cells and Cdc42 activation in vitro. Nat Chem Biol. 2006 ;2:39-46.
Penning, TD; Talley, JJ; Bertenshaw, SR; Carter, JS; Collins, PW; Docter, S; Graneto, MJ; Lee, LF; Malecha, JW; Miyashiro, JM; Rogers, RS; Rogier, DJ; Yu, SS; Anderson, GD; Burton, EG.; Cogburn, JN; Gregory, SA; Koboldt, CM; Perkins, WE; Seibert, K; Veenhuizen, AW; Zhang, YY; Isakson, PC. Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib). J. Med. Chem. 1997: 40: 1347-1365.
Raftopoulou M, Hall A. Cell migration: Rho GTPases lead the way. Dev Biol. 2004; 265:23-32.
Ridley AJ. Rho GTPases and actin dynamics in membrane protrusions and vesicle trafficking. Trends Cell Biol. 2006; 16, 522-529.
Rossman KL, Der CJ, Sondek J. GEF means go: turning on RHO GTPases with guanine nucleotideexchange factors. Nat Rev Mol Cell Biol. 2005;6:167-80.
Sahai E, Marshall CJ. RHO-GTPases and cancer. Nat Rev Cancer. 2002;2:133-42.
Schwartz SL, Tessema M, Buranda T, Pylypenko O, Rak A, Simons PC, Surviladze Z, Sklar LA, Wandinger-Ness A. Flow cytometry for real-time measurement of guanine nucleotide binding and exchange by Ras-like GTPases. Anal Biochem. 2008;381:258-66.
Shutes A, Onesto C, Picard V, Leblond B, Schweighoffer F, Der CJ. Specificity and mechanism of action of EHT1864, a novel small molecule inhibitor of Rac family small GTPases. J. Biol. Chem. 2007;282:35666-78.
Surviladze Z, Dráberová L, Kubínová L, Dráber P. Functional heterogeneity of Thy-1 membrane microdomains in rat basophilic leukemia cells. Eur J Immunol. 1998;28:1847-58.
Surviladze Z, Waller A, Wu Y, Romero E, Edwards BS, Wandinger-Ness A, Sklar LA. Identification of a small GTPase inhibitor using a high-throughput flow cytometry bead-based multiplex assay. J. Biomol. Screen. 2010;15:10-20.
Takai Y, Sasaki T, Matozaki T. Small GTP-binding proteins. Physiol Rev. 2001;81:153-208.
Van den Broeke C, Radu M, Chernoff J, Favoreel HW. An emerging role for p21-activated kinases (Paks) in viral infections. Trends Cell Biol. 2010; 20:160-169.
Van Hennik PB, Hordijk PL. Rho GTPases in hematopoietic cells. Antioxid Redox Signal. 2005;7:1440-55.
Vega FM, Ridley AJ. Rho GTPases in cancer cell biology. FEBS Lett. 2008; 582:2093-101.
Wilson BS, Seagrave J, Oliver JM. Impaired secretion and increased insolubilization of IgE-receptor complexes in mycophenolic acid-treated (guanine nucleotide-depleted) RBL-2H3 mast cells. J Cell Physiol. 1991;149:403-7.
Yang L, Wang L, Zheng Y. Gene targeting of Cdc42 and Cdc42GAP affirms the critical involvement of Cdc42 in filopodia induction, directed migration, and proliferation in primary mouse embryonic fibroblasts. Mol Biol Cell. 2006; 17:4675-85.
Zhang B, Zhang Y, Shacter E, Zheng Y. Mechanism of the guanine nucleotide exchange reaction of Ras GTPase—evidence for a GTP/GDP displacement model. Biochemistry. 2005; 44:2566-76.
Wiley, R.H.; C.H. Jarboe; F.N. Hayes; E. Hansbury; J.T. Nielsen; P.X. Callahan; and M.C. Sellars; 1,3,5-Triaryl-2-pyrazolines for Use as Scintillation Solutes. J. Org. Chem. 1958; 23:732-738.
Levai, A. and Jeko, J.; Synthesis of carboxylic acid derivatives of 2-pyrazolines. ARKIVOC 2007 (i) 134-145.
Winum, J.-Y.; J.-M. Dogne; A. Casini; X. de Leval; J-L. Montero; A. Scozzafava; A. Vullo; A. Innocenti; and C. T. Supuran; Carbonic Anhydrase Inhibitors: Synthesis and Inhibition of Cytosolic/Membrane-Associated Carbonic Anhydrase Isozymes I, II, and IX with Sulfonamides Incorporation Hydrazino Moieties. J. Med. Chem. 2005, 48, 2121-2125.
Surviladze, Z; A. Waller; J. J. Strouse; C. Bologa; O. Ursu; V. Sales; J.F. Parkinson; G. K. Phillips; E. Romero; A. Wandinger-Ness and L.A. Sklar; C. Schroeder; D. Simpson; J. Noth; J. Wang; J. Golden and J. Aube; A Potent and Selective Inhibitor of Cdc42 GTPase. Probe Reports from the NIH Molecular Libraries Program [Internet]. Bethesda (MD): National Center for Biotechnology Information (US); 2010-. Feb. 27, 2010 [updated Dec. 16, 2010].
Lohani, S. (2006) Understanding nucleation process in the crystallization of polymorphs. (Doctoral Dissertation) Retrieved from ProQuest Dissertations and Thesis (Assession Order No. AAT3234930).
Morissette, S. L. Almarsson, O. et al., High-throughput crystallization: polymorphs, salts, co-crystals, and solvates of pharmaceutical solids. Advanced Drug Delivery Reviews. Feb. 2004; 56; 275-300.
Rathish, I.G. et al. Synthesis and antiinflammatory activity of some new 1,3,5-trisubstituted pyrazolines bearing benzene sulfonamide. Bioorganic & Medicinal Chemistry Letters, 2009, 19, 255-258.
Chemical Abstract Registry No. 1222513-26-9, indexed in the Registry File on STN CAS Online May 12, 2010.
Chemical Abstract Registry No. 1222662-08-9, indexed in the Registry File on STN CAS Online May 13, 2010.
Chemical Abstract Registry No. 1222662-46-5, indexed in the Registry File on STN CAS Online May 13, 2010.
Mroszczak E, et al. Chiral Kinetics and Dynamics of Ketorolac. J Clin Pharmacol, 1996;36:521-539.
Duggan, et al. Molecular Basis for Cyclooxygenase Inhibition by the Non-steroidal Anti-inflammatory Drug Naproxen. Journal of Biological Chemistry, 2010;285(45):34950-34959.
Handley DA, et al. Preclinical Enantioselective Pharmacology of (R)- and (S)-Ketorolac. J Clin Pharmacol, 1998;38:25S-35S.

(56) References Cited

OTHER PUBLICATIONS

Penning TD, et al. Synthesis and Biological Evaluation of the 1,5-Diarylpyrazole Class of Cyclooxygenase-2 inhibitors: Identification of 4-[5-(4-Methylphenyl)-3-(trifluoromethyl)-1H-pyrazol-1-yl]benzenesulfonamide (SC-58635, Celecoxib). J Med Chem, 1997;40:1347-1365.

Reyners AKL, et al. A randomized phase II study investigating the addition of the specific COX-2 inhibitor celecoxib to docetaxel plus carboplatin as first-line chemotherapy for stage IC to IV epithelial ovarian cancer, Fallopian tube or primary peritoneal carcinomas: the DoCaCel study. Annals of Oncology, 2012;23:2896-2902.

Legge F, et al. Phase II study of the combination carboplatin plus celecoxib in heavily pre-treated recurrent ovarian cancer patients. BMC Cancer, 2011;11:214-223.

Hong L, et al. Characterization of a Cdc42 protein inhibitor and its use as a molecular probe. Journal of Biological Chemistry, 2014;289:6837.

Youssef AM, et al. Synthesis and biological evaluation of novel pyrazole compounds. Bioorganic & Medicinal Chemistry, 2010;18:5685-5696.

Hong L, et al. Characterization of a Cdc42 Protein Inhibitor and Its Use as a Molecular Probe. The Journal of Biological Chemistry, 2013;288(12):8531-8543.

Insuasty B, et al. Synthesis of novel pyrazoic analogues of chalcones and their 3-aryl-4-(3-aryl-4,5-dihydro-1H-pyrazol-5-yl)-1-phenyl-1H-pyrazole derivatives as potential antitumor agents. Bioorganic & Medicinal Chemistry, 2010;18:4965-4974.

Lee JP, et al. Selective cyclooxygenase inhibitors increase paclitaxel sensitivity in taxane-resistant ovarian cancer by suppressing P-glycoprotein expression. J Gynecol Oncol, 2013;24(3):273-279.

Guo Y, et al. R-Ketorolac Targets Cdc42 and Rac1 and Alters Ovarian Cancer Cell Behaviors Critical for Invasion and Metastasis. Mol Cancer Ther, 2015;14(10):2215-2227.

Saga Y, et al. Comparison of demetalation properties between zinc chlorine and zinc porphyrin derivatives: Effect of macrocyclic structures. Bioorganic & Medicinal Chemistry, 2010;18:5697-5700.

Ushijima K, et al. Treatment for Recurrent Ovarian Cancer—At First Relapse. Journal of Oncology, 2010; Article ID 497429, doi:10.115/2010/497429.

* cited by examiner

FIGURE 1C
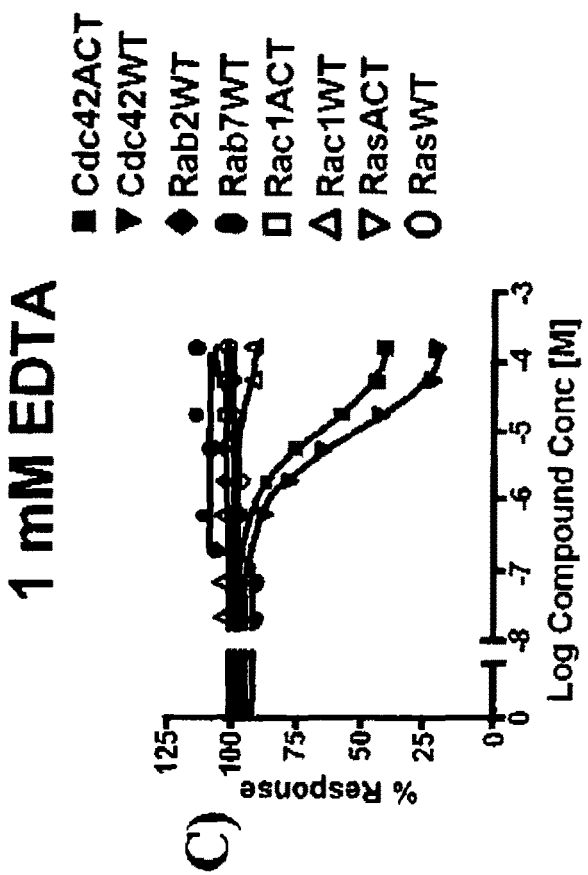
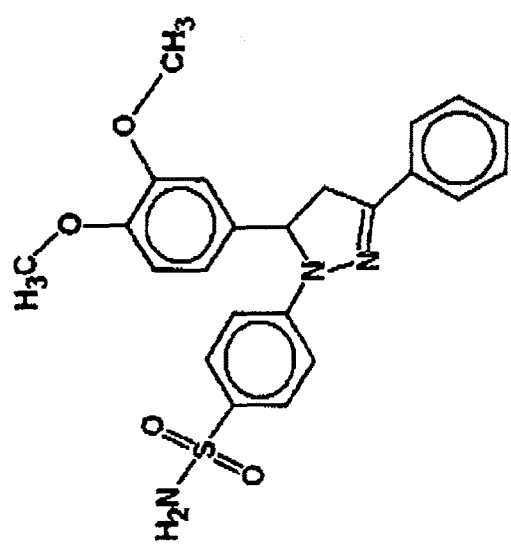

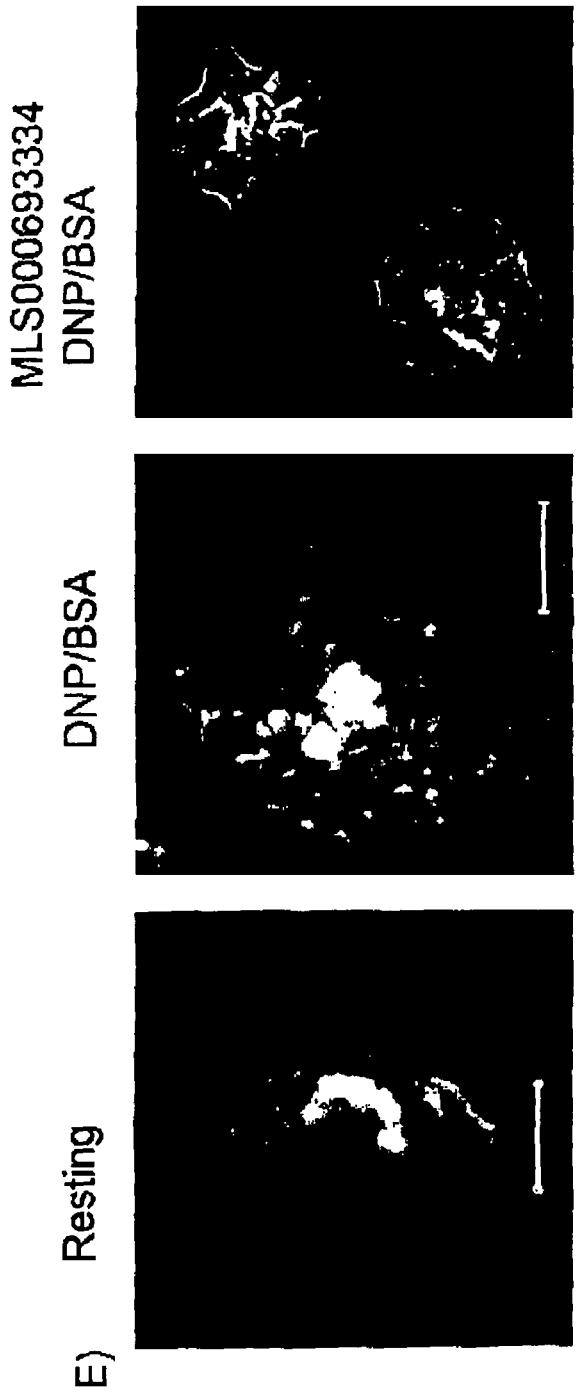

FIGURE 4C and 4D
4C
4D

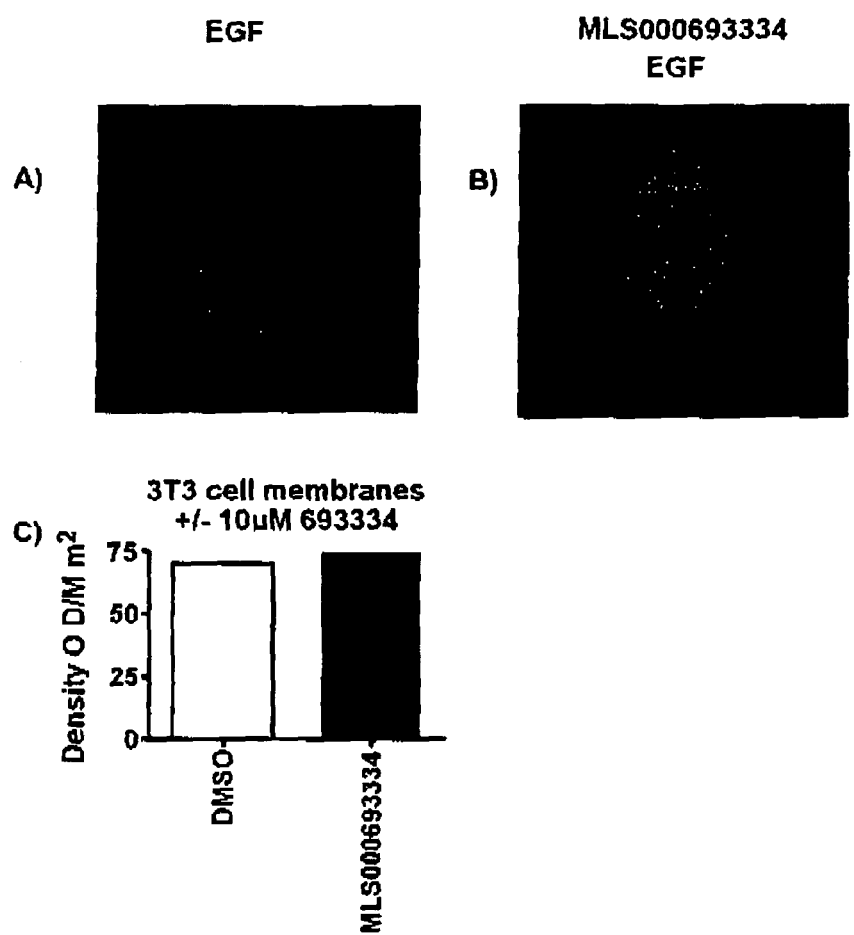

FIGURE 6
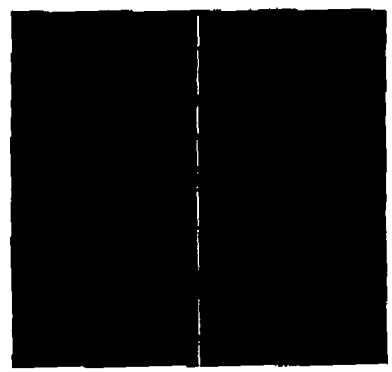
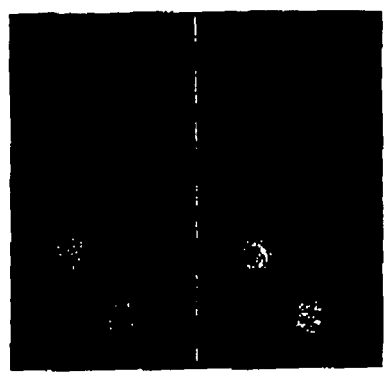

SB202190

C)

Cdc42 wt binding bodipy-GTP in the presence of SB 202190 (1mM EDTA NP-HPS)

D)

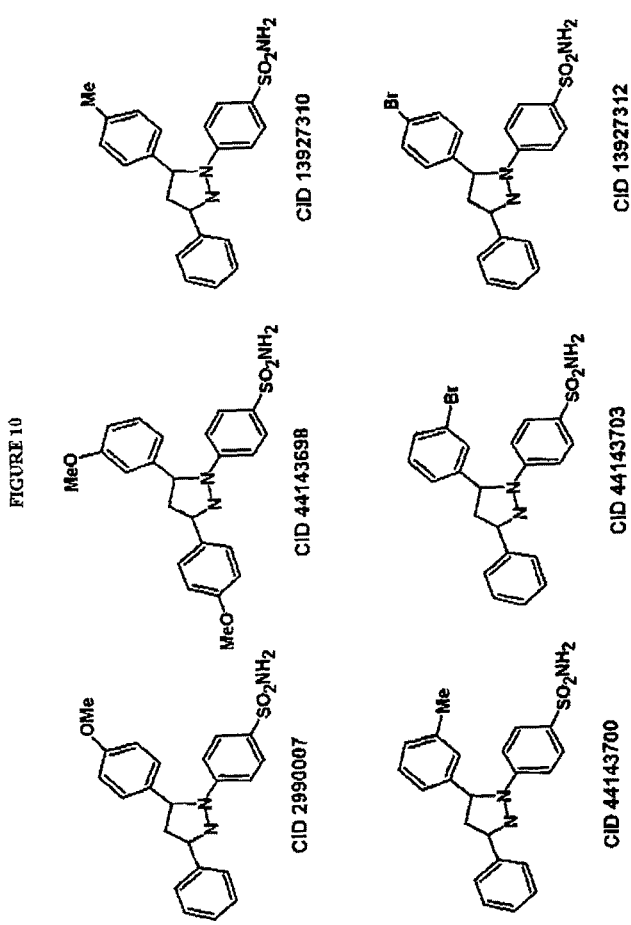

MODULATORS OF GTPASE AND USE IN RELEVANT TREATMENT

RELATED APPLICATIONS, CLAIM FOR PRIORITY AND GRANT SUPPORT

The present application claims the benefit of priority from and is a divisional application of U.S. patent application Ser. No. 13/161,832, filed Jun. 16, 2011, entitled "Modulators of GTPase and Use in Relevent Treatment", which claims the benefit of priority from provisional application No. 61/397,864, filed Jun. 17, 2010, entitled "Ras-related GTPases as Targets of Non-Steroidal Anti-inflammatory Drugs", both which are incorporated by reference in their entirety herein.

This invention was made with government support under grants U54MH074425, U54MH084690, R03MH081231, U54HG005031 and P30CA118100 awarded by the National Institutes of Health. The government has certain rights in the invention.

FIELD OF THE INVENTION

The present invention relates to molecules which function as selective modulators (i.e., inhibitors and agonists, preferably inhibitors) of the Ras-homologous (Rho) family of small GTPases, in particular, Cdc42 GTPase and their use to treat diseases, for example cancers, including metastatic cancer (e.g., especially B-cell lymphoma, stomach cancer including gastric adenocarcinoma, leukemias, including myeloid and B-cell leukemias, breast, cervical, testicular and prostate cancer among others where Cdc42 GTPase is overexpressed or hyperactivated), genetic and acquired diseases where activation of Cdc42 GTPase plays a pivotal role (e.g., neurodegenerative diseases, including Alzheimer's disease, Huntington's disease, Parkinson's disease, amyotrophic lateral sclerosis (ALS or Lou Gehrig's disease), rheumatoid arthritis, atherosclerosis, diabetes type I, autosomal polycystic kidney disease, cystic kidney disease, precystic kidney disease, microbial infections, including *Chlamydia* infections, *E. coli* infections, *H. pylori* infections and its secondary effects including gastric ulcers, *Coxiella Brunetti* (Q-fever) infections and *Streptococcus pneumonia* infections, fungal infections including *Paracoccidiodes brasiliensis* and *Candida albicans* and their secondary effects including lung edema. Additionally, compounds according to the present invention may be used to inhibit rejection (graft host response) in transplant patients (pursuant to transplantation), to promote immunosuppression, anti-inflammatory response and to mobilize stem cell (migration) in patients in need, among others.

BACKGROUND OF THE INVENTION

The Ras-homologous (Rho) family of small GTPases (Rac, Cdc42 and Rho) are key regulators of actin reorganization, cell motility, cell-cell and cell-extracellular matrix (ECM) adhesion as well as of cell cycle progression, gene expression and apoptosis (FIG. 1) [1-8]. In many human cancers (including colon and breast), aberrant Rho-family signaling due to changes in the GTPase itself or in its regulation loops is a critical underpinning of tumor growth and survival, invasion and metastasis [9-13] (FIG. 1). RhoA and RhoC correlate with advanced ovarian cancer and peritoneal dissemination [14; 15]. Although Rac1 and Cdc42 have been recognized as attractive therapeutic targets, specific Rac GTPase inhibitors while effective in culture [16; 17] have not been translated to clinical use and there are no established Cdc42 specific inhibitors. Lovastatin was shown to inhibit Rho GTPase and reduce ovarian metastasis in a xenograft model [15]. However, the use of statins to block GTPase membrane association has met with only modest success due to their broad spectrum inhibition of protein prenylation resulting in pleiotropic effects on many GTPases and pathways [18]. Furthermore, recent animal studies wherein the effects of geranylgeranyltransferase type I deficiency were analyzed revealed an unexpected hyperactivation of Rho GTPases and concomitant severe joint inflammation {Khan, 2011}. Thus, more specific agents for clinical application for use as inhibitors of Cdc42 GTPase are urgently needed. The present invention seeks to meet that need.

Objects of the Invention

It is an object of the invention to provide compounds for modulating Rho family GTPase, in particular, Cdc42 GTPase in patients or subjects.

It is another object of the invention to treat disease states and/or conditions which are medicated through targeting of Rho family GTPase, in particular Cdc42 GTPase.

It is yet another object of the invention to provide pharmaceutical compositions which may be used to modulate, especially inhibit Cdc42 GTPase in patients or subjects.

It is still a further object of the invention to treat cancer, especially ovarian cancer and other cancers where GTPase is overexpressed or hyperactivated utilizing compounds, compostions and/or methods which are presented herein.

It is an additional object of the invention to provide methods for treating genetic and acquired diseases where activation of Cdc42 GTPase plays a role including in Alzheimer's disease, Huntington's disease, Parkinson's disease, amyotrophic lateral sclerosis (ALS or Lou Gehrig's disease), rheumatoid arthritis, atherosclerosis, diabetes type I, autosomal dominant polycystic kidney disease, cystic kidney disease and precystic kidney disease.

It still another object of the invention to inhibit and/or treat *Chlamydia* infections, *E. coli* infections, *H. pylori* infections and its secondary effects including gastric ulcers, *Coxiella Brunetti* (Q-fever) infections and *Streptococcus pneumonia* infections, fungal infections including *Paracoccidiodes brasiliensis* and *Candida albicans* and their secondary effects including lung edema.

It is yet another object of the invention to provide compounds which may be used to inhibit rejection (graft host response) in transplant patients, to promote immunosuppression, anti-inflammatory response and to mobilize stem cell (migration), among others.

Any one or more of these and/or other objects of the invention may be readily gleaned from a description of the invention which follows.

BRIEF DESCRIPTION OF THE INVENTION

The present invention relates to compounds according to the chemical structure I

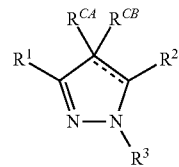

Wherein $R^1$ and $R^2$ are each independently an optionally substituted aryl group, preferably a phenyl group which is optionally substituted;
$R^3$ is a phenyl group which is substituted with an ortho, meta or para sulfonamide group (preferably, a para sulfonamide group) according to the chemical structure

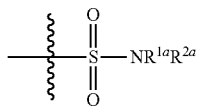

Where $R^{1a}$ and $R^{2a}$ are each independently H or a $C_1$-$C_4$ alkyl group (preferably H or methyl, more preferably H) which may be optionally substituted with a hydroxyl group, wherein $R^3$ may be further optionally substituted;
$R^{CA}$ is H or a $C_1$-$C_4$ alkyl group which is optionally substituted with a hydroxyl group; and
$R^{CB}$ is absent H or a $C_1$-$C_4$ alkyl group which is optionally substituted with a hydroxyl group (preferably, both $R^{CA}$ and $R^{CB}$ are H),
Or a pharmaceutically acceptable salt, enantiomer, diasteromer, solvate or polymorph thereof.

In certain preferred aspects of the invention, the compound is according to the chemical structure II

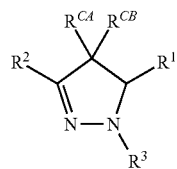

Where $R^1$ and $R^2$ are the same as described above;
$R^3$ is a phenyl group which is substituted with a para-sulfonamide group

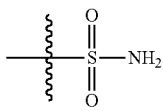

and may be further optionally substituted; and
$R^{CA}$ and $R^{CB}$ are both H, or
a pharmaceutically accept salt, enantiomer, solvate or polymorph thereof.

In still additional aspects of the invention, the compound is according to the chemical structure III:

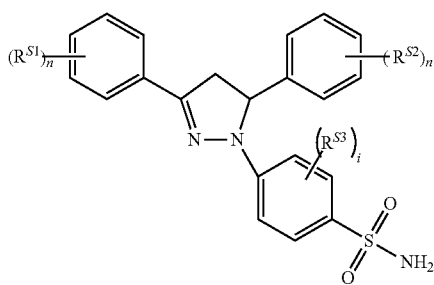

Where $R^{S1}$, $R^{S2}$ and $R^{S3}$ are each independently H, an optionally substituted $C_1$-$C_{10}$ (preferably, $C_1$-$C_6$) alkyl group (preferably methyl or isopropyl), a halogen (F, Cl, Br, I, preferably F), hydroxyl, a cyano group, a nitro group, an optionally substituted acyl ($C_1$-$C_{10}$) an optionally substituted $C_1$-$C_{10}$ (preferably $C_1$-$C_6$) alkoxy group, an optionally substituted $C_2$-$C_{10}$ ester (oxycarbonyl ester or carbonyloxyester) group, an optionally substituted $C_2$-$C_{10}$ ether group, an optionally substituted $C_2$-$C_{10}$ alkoxyether group, a carboxamido group (optionally substituted with one or two $C_1$-$C_6$ alkyl groups), aminocarbonyl (optionally substituted with a $C_1$-$C_6$ alkyl group), thioamido (optionally substituted with one or two $C_1$-$C_6$ alkyl groups), azido, $C_2$-$C_{10}$ (preferably $C_2$-$C_6$) alkenyl or alkynyl (preferably alkynyl), amino, ($C_1$-$C_6$) alkyl and dialkyl amino, aryloxy, thio, ($C_1$-$C_6$) thioether or a ($C_3$-$C_9$) monocyclic or bicyclic heterocyclic group, among others; n is 0, 1, 2 or 3 and i is 0, 1 or 2, or a pharmaceutically accept salt, enantiomer, solvate or polymorph thereof.

In preferred aspects of the invention, $R^{S1}$ and $R^{S2}$ are independently H, halogen (preferably, Br or Cl, more preferably Br), a $C_1$-$C_4$ alkyl group (preferably methyl) or a $C_1$-$C_6$ alkoxy (preferably methoxy) group, $R^{S3}$ is H, n is 0 or 1 and i is 0.

Additional preferred compounds according to the present invention include the following compounds or their pharmaceutically acceptable salts, enantiomers, solvates or polymorphs thereof:

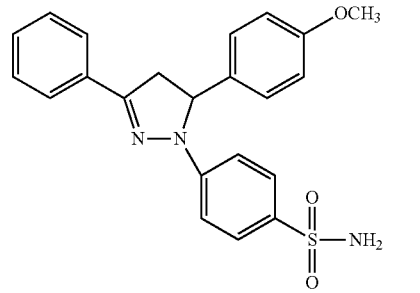

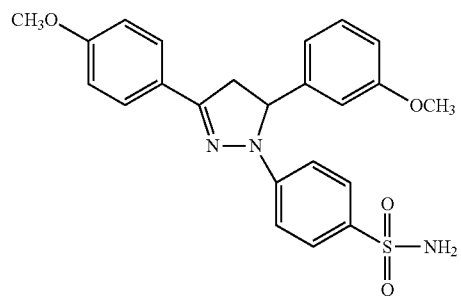

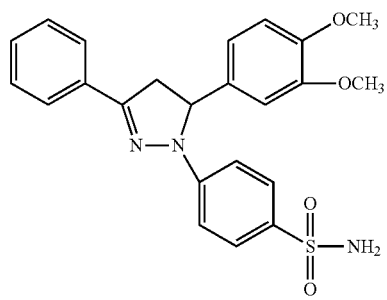

-continued

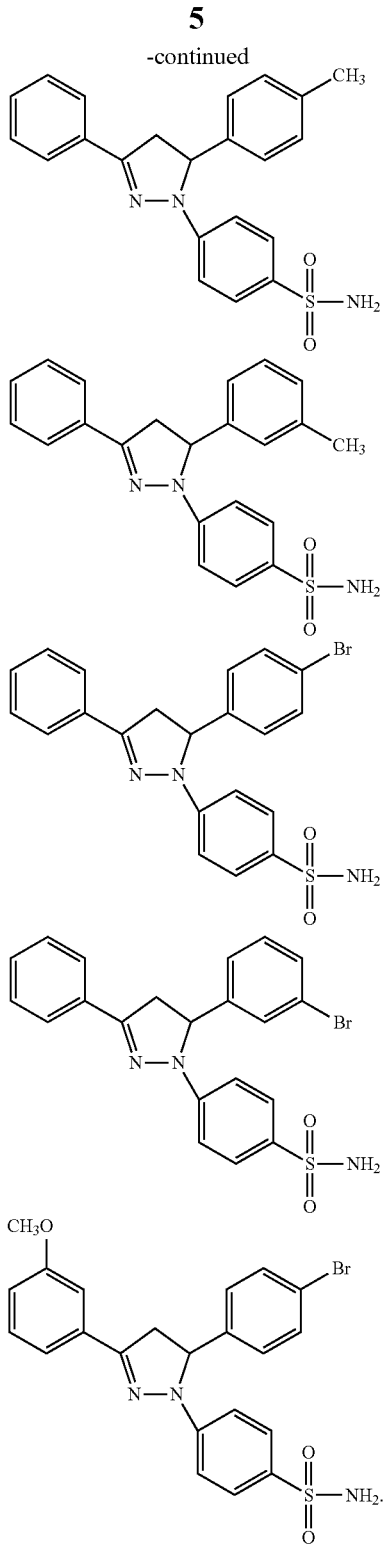

The present invention also relates to a pharmaceutical composition comprising an effective amount of one or more compounds as described hereinabove in combination with a pharmaceutically acceptable additive, carrier or excipient and optionally in combination with an additional bioactive agent, preferably an anticancer agent as otherwise disclosed herein.

The compounds which are disclosed herein find use to treat cancers, including solid and epithelial tumors (e.g., especially B-cell lymphoma, stomach cancer including gastric adenocarcinoma), leukemias, including myeloid and B-cell leukemias, breast, cervical, testicular and prostate cancer, among numerous others where Cdc42 GTPase is overexpressed or hyperactivated), genetic and acquired diseases where activation of Cdc42 GTPase plays a pivotal role (e.g., neurodegenerative diseases, including Alzheimer's disease, Huntington's disease, Parkinson's disease, amyotrophic lateral sclerosis (ALS or Lou Gehrig's disease), rheumatoid arthritis, atherosclerosis, diabetes type I, autosomal dominant polycystic kidney disease, cystic kidney disease, precystic kidney disease, microbial infections, including *Chlamydia* infections, *E. coli* infections, *H. pylori* infections and its secondary effects including gastric ulcers, *Coxiella Brunetti* (Q-fever) infections and *Streptococcus pneumonia* infections, fungal infections including *Paracoccidiodes brasiliensis* and *Candida albicans* and their secondary effects including lung edema. Additionally, compounds according to the present invention may be used to inhibit rejection (graft host response) in transplant patients (pursuant to transplantation), to promote immunosuppression, anti-inflammatory response and to mobilize stem cell (migration) in patients in need, among others.

Accordingly, the present invention relates to a method for modulating, including inhibiting a GTPase in a patient or subject in need of modulation wherein the GTPase is, in particular, a Cdc42 GTPase, the method comprising administering to said patient or subject an effective amount of a compound as set forth hereinabove. The modulator is preferably an antagonist of GTPase. The present invention also relates to methods for modulating disease and/or conditions which are mediated through Cdc42 GTPase, including treating and/or inhibiting the progression of neurologic and inflammatory diseases dependent on Cdc42 GTPase such as rheumatoid arthritis, atherosclerosis, diabetes (type I), Huntington's disease, Alzheimer's disease, Parkinson's disease, amyotrophic lateral sclerosis (ALS or Lou Gehrig's disease), rheumatoid arthritis, atherosclerosis, diabetes type I, autosomal dominant polycystic kidney disease, cystic kidney disease, precystic kidney disease, as well as microbial infections in which Cdc42 GTPase plays an important/pivotal role, including *Chlamydia* infections, *E. coli* infections, *H. pylori* infections and its secondary effects including gastric ulcers, *Coxiella Brunetti* (Q-fever) infections and *Streptococcus pneumonia* infections, fungal infections including *Paracoccidiodes brasiliensis* and *Candida albicans* and their secondary effects including lung edema. Additionally, compounds according to the present invention may be used to inhibit rejection (graft host response) in transplant patients (pursuant to transplantation), to promote immunosuppression, anti-inflammatory response and to mobilize stem cell (migration) in patients in need, among others.

BRIEF DESCRIPTION OF THE FIGURES

FIG. 1 B shows six Rho family GTPases (Rac1Q61L (act and wild type (wt); Cdc42Q61L (act_ and wild-type (wt); RhoAQ63L (act) and wild type (wt)) in the presence of 1 mM Mg2+ and 1 nM BODIPY-FL-GTP.

FIG. 1 C shows inhibition profile of MLS00069339 against eight GTPase targets Cdc42Q611 (act) and wild-type (wt); Rab2; Rab7 RacQ61L (act) and wild-type (wt); Harvey, H-RasG12V (act and wild type (wt)) in the presences of 1 mM EDTA and 100 nMBODIPY-FL-GTP.

FIG. 1 D shows dose-response analysis of MLS00069339 examined in the presence of NP-HPS buffer containing 1 mM EDTA.

FIG. 1 E shows dose-response analysis of MLS00069339 examined in the presence of NP-HPS buffer containing 1 mM $MgCl_2$.

Assays were performed holding the inhibitor concentration constant at 10 µM and monitoring kinetics of BODIPY-GTP binding over a >10-fold concentration range (3-100 nM GTP) in the presence of 1 mM EDTA. The presence of the small molecule inhibitor mainly decreased the $B_{max}$ of GTP-binding, while the affinity of GTP to wild type Cdc42 ($K_d$~40 nM) decreased slightly ($K_d$~50 nM).

Figures 2A, 2B:
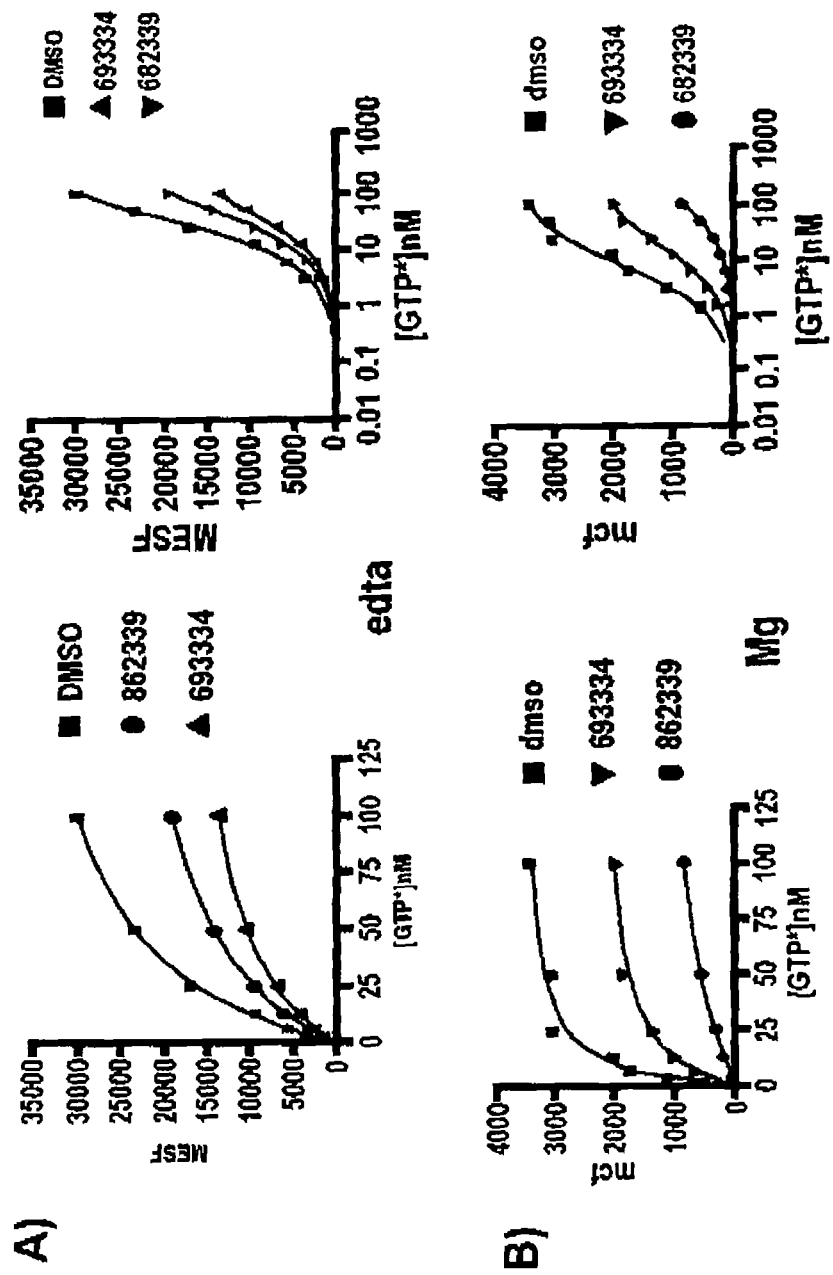
FIG. 2 A shows equilibrium binding assays of BODIPY-FL-GTP in the presence or absence of MLS000693334 and MLS000862339 that were performed using wild-type Cdc42.
Figures 2C, 2D:
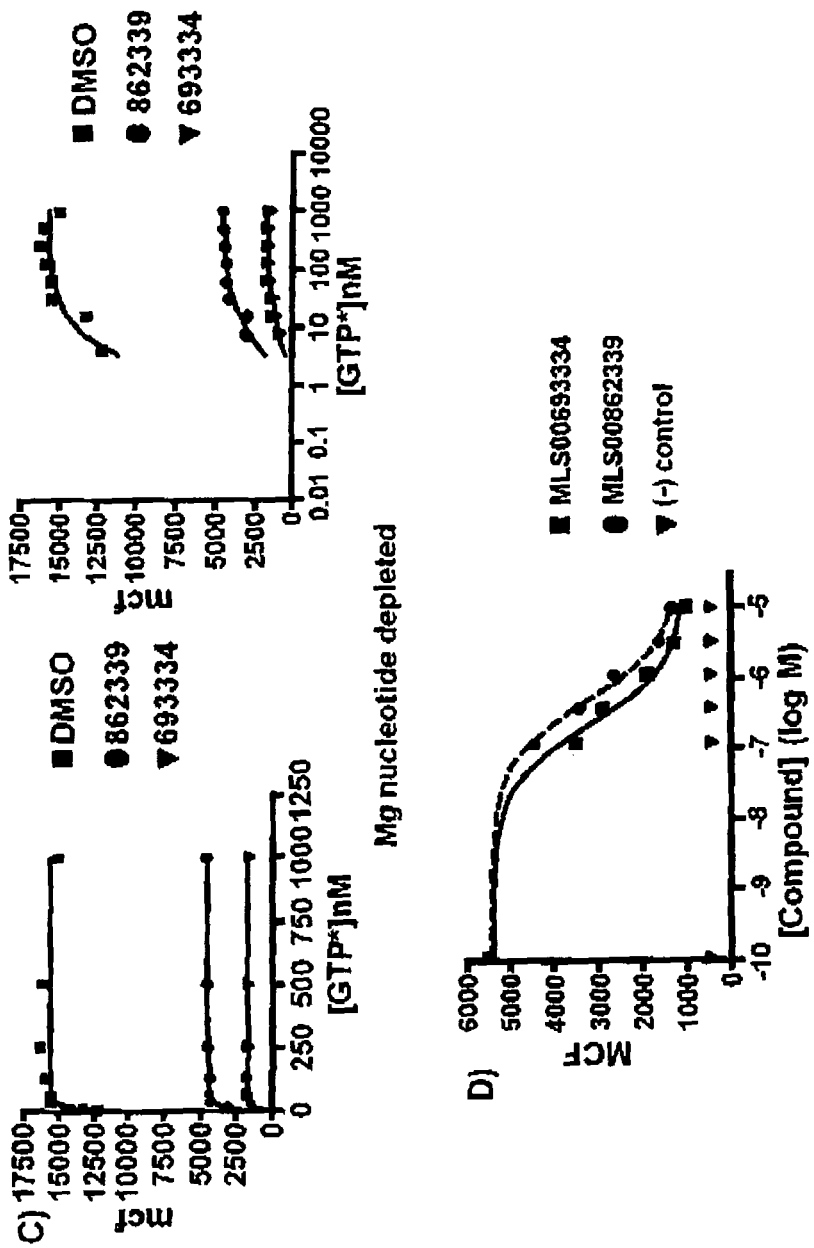

FIG. 2 B shows equilibrium binding being measured in the presence of 1 mM $MgCl_2$. Both inhibitors mainly decrease $B_{max}$. It looks like that MLS000862339 significantly increases $K_d$, but same results analyzes in Log scale shows that concentration of substrate (BODIPY-FL-GTP) is not close to saturation and should be increased to get reliable result. For this reason we performed equilibrium binding experiments in broader range of fluorescently labeled GTP. But preliminary we depleted bead-anchored Cdc42 wt from endogenous nucleotide.

FIG. 2 C shows both Cdc42 specific inhibitors have no effect on substrate binding and decreases $B_{max}$ indicating that they are acting like typical non-competitive inhibitors.

FIG. 2 D shows the detection of $IC_{50}$ we performed equilibrium binding experiments holding constant (1.5 nM) the substrate concentration and various concentration of inhibitors in the presence of 1 mM $MgCl_2$. Inhibition of fluorescent GTP binding to Cdc42 wt in the presence of inhibitors analyzed by Prizm software shows $IC_{50}$ for MLS000693334 is 200 nM, and 400 nM for MLS000862339

Figures 3A, 3B:
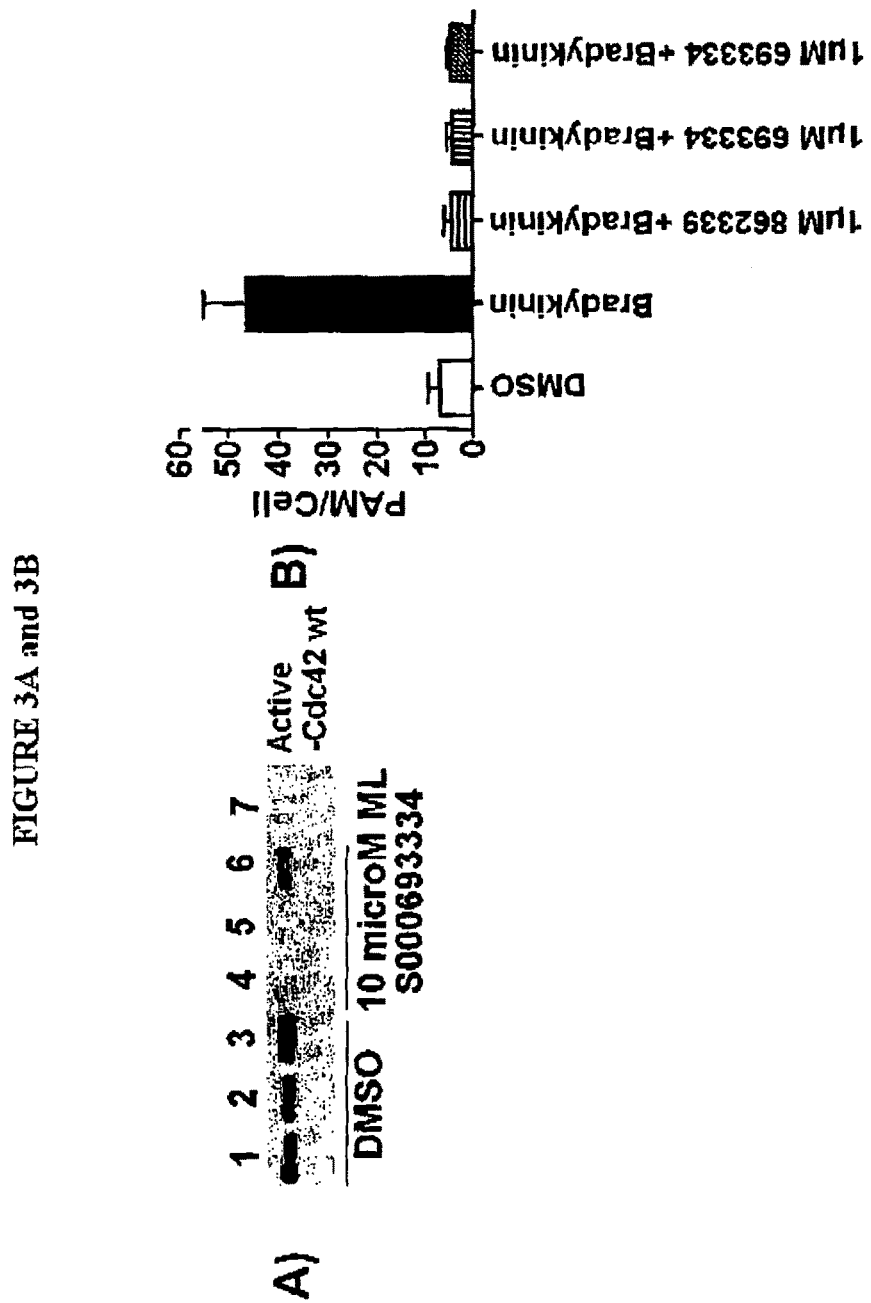

FIG. 3A shows that in the presence of 10 µM inhibitor, complex formation was dramatically reduced. The inventors examined the effect of MLS000693334 on binding of active Cdc42 to Pak-PBD. For in vitro analyses, we used purified recombinant His-Cdc42. Enzyme was incubated with indicated concentration of GTPγS (to prevent hydrolysis during the assay) in the presence or absence of 10 µM MLS000693334. The fraction of active Cdc42(GTPγS) was identified by binding to GST-PAK-PBD immobilized on glutathione beads and western blot analysis of bound Cdc42.

Figure 3C:
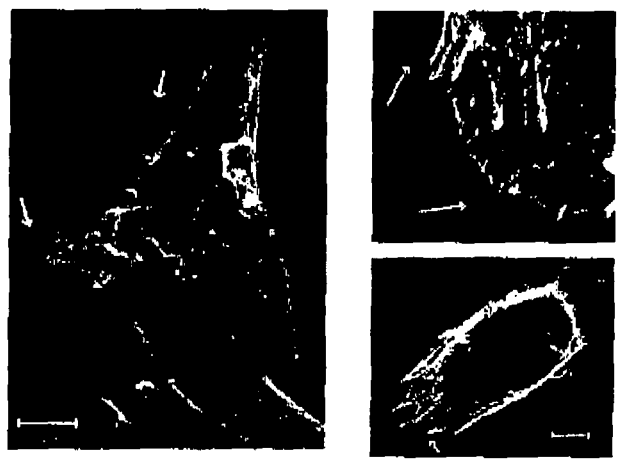
Figure 3D:
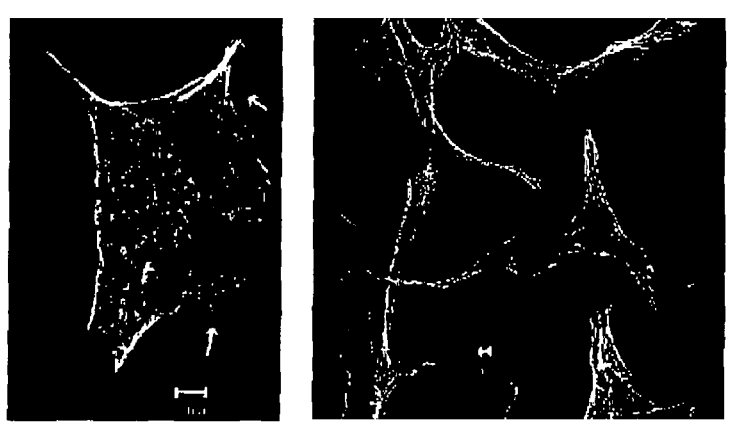

FIG. 3 B shows numbers of microspikes greater than 1 µm in length were estimated in randomly chosen at least 10 cells and experiments were repeated twice. Confocal microscopy studies revealed that filopodia formation by bradykinin treatment was significantly reduced if Swiss 3T3 cells were preliminary incubated with Cdc42 specific inhibitor.

FIGS. 3 C and D show that 1 h treatment of starved fibroblasts with 10 µM inhibitor dramatically reduces number of microspikes.

FIG. 3 E shows that even cross-linking of FcεRI receptors does not induce flattening and ruffling in the presence of inhibitors, while cross-linking of receptors in the absence of inhibitor initiates formation of filopodia.

Figure 4A:
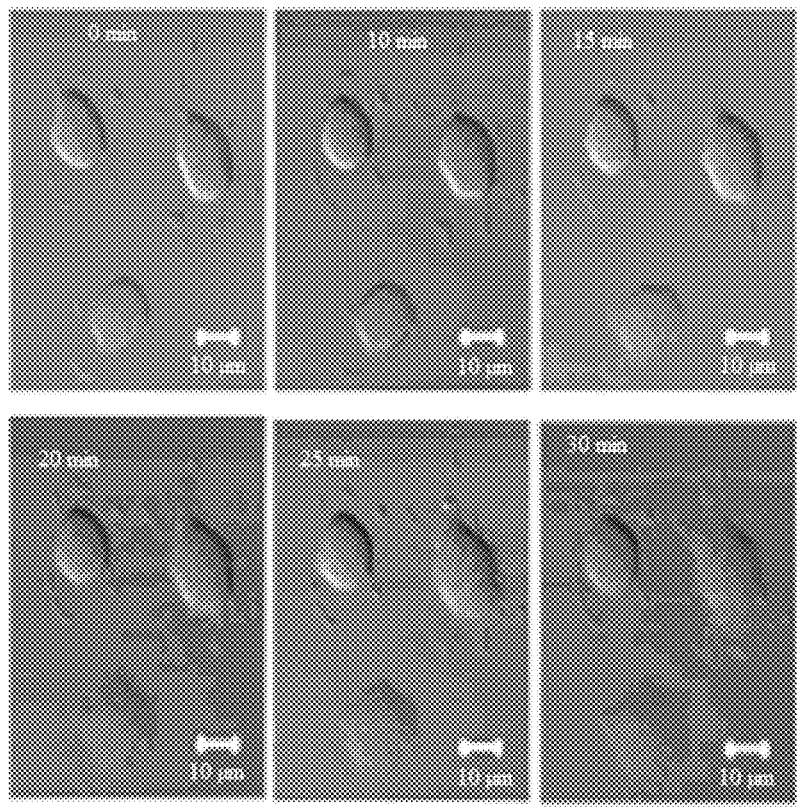
Figure 4B:
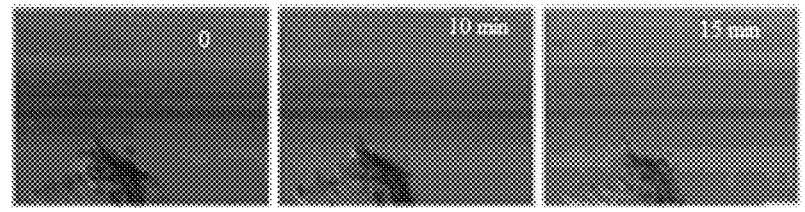

FIG. 4 A shows effect of Cdc42 specific inhibitors on RBL cells morphology after activation of cells via two different pathways. As expected cross-linking of IgE receptors via DNP/BSA induced RBL cell flattening, filopodia and lamellipodia formation FIG. 4 B shows inhibition of filopodia formation and cell spreading; however there was no inhibition of lamellipodia formation.

FIG. 4 C shows that activation of RBL cells via Thy-1 pathway induced cell flattening, ruffling and formation of lamellipodia and filopodia and surface ridges were enhanced after 5-20 min. After 30 min most cells were flattened, indicating good activation.

FIG. 4 D shows that resting RBL-2H3 cells treated with 10 µM MLS000693334 showed no change in morphology and cross-linking of Thy-1 molecules in inhibitor treated cells dramatically inhibits filopodia formation and cell spreading.

FIG. 5 A shows Cdc42 distribution in starved Swiss 3T3 cells in the presence or absence of Cdc42 specific inhibitors. It is known and it was confirmed with experiments, that Cdc42, after treatment of fibroblasts with EGF, is getting activated and is recruited to the plasma membrane FIG. 5 B shows an EGF induced localization of Cdc42 on the membrane that was not treated with 1 µM MLS000693334 treated Swiss 3T3 cells This reduced membrane localization after treatment with the inhibitor could be the result of inhibition of recruitment of enzyme to the membrane or increased dissociation of active Cdc42 from the membrane. To investigate if MLS000693334 effects dissociation of Cdc42 from membrane we used membrane fraction of Swiss 3T3 cells grown in media with 10% serum. In the presence of serum Cdc42 is activated, and is bound to membrane. Membrane-rich fraction incubated with DMSO (vehicle) or 10 µM MLS000693334 for 1 h. Membrane fraction washed and content of Cdc42 in membranes analyzed by Western-blot.

FIG. 5 C shows that inhibitor has not increased dissociation of active form of enzyme from membrane.

FIG. 6 A shows resting cells wherein actin is distributed mainly at the plasma membrane. Cdc42 is distributed randomly. Cells were starved only for 2 h, but still medium contained 0.1% BSA. In this conditions part of Cdc42 molecules are still active and co-localized on plasma membrane.

FIG. 6 B shows Activation of RBL cells by cross-linking of FcεRI causes a remarkable transformation in cell surface topography. Cells are getting well ruffled and actin enriched protrusions appeared on the cell plasma membrane. Cdc42 is getting patched and co-localization on membrane is increased FIG. 6 C shows 1 h treatment of RBL cells with Cdc42 specific inhibitor, before activation dramatically changes figure of actin and Cdc42 distribution. FcεRI-cross-linked dependent membrane ruffling diminished, and Cdc42 recruitment to plasma membrane is also blocked and enzyme is localized perinucleary, although Cdc42 patches, characteristic to IgE receptor activation is still observed.

Figures 7A, 7B:
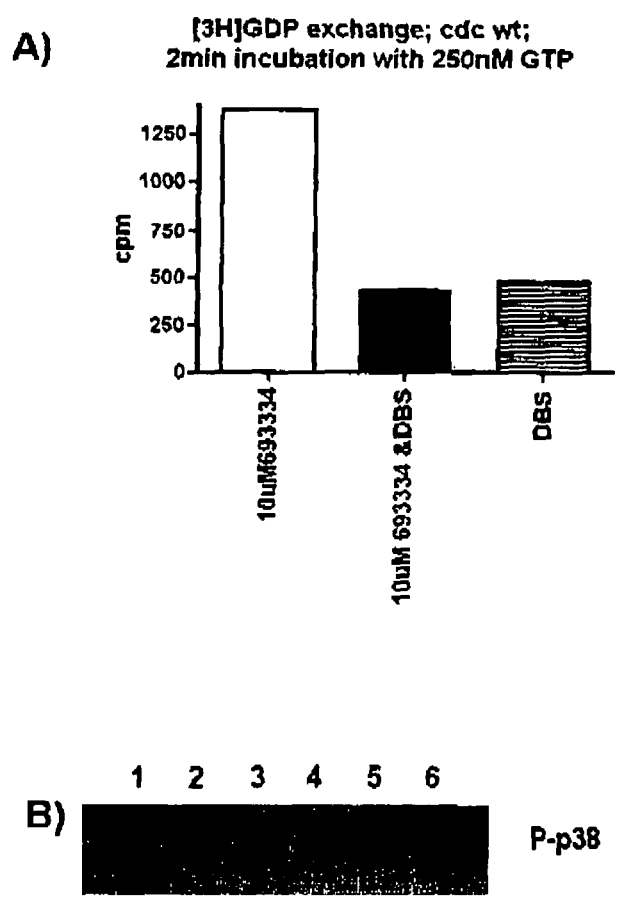
Figure 7C:
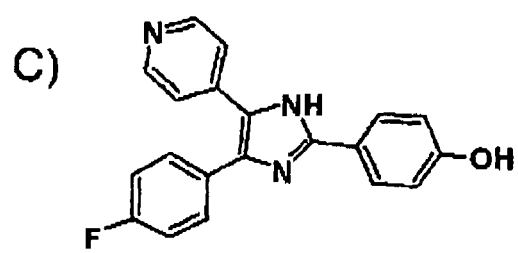
Figure 7D:
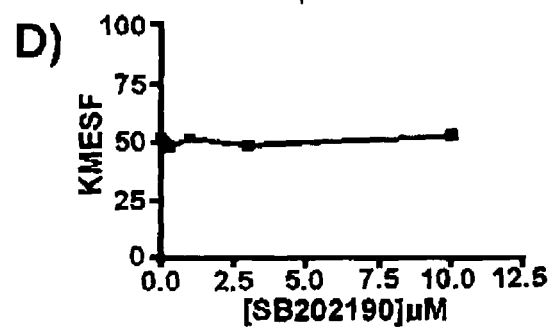

FIG. 7 A shows that the incubation of 10 µM MLS000693334 with Cdc42 did not changes Dbs activity, indicating that Cdc inhibitor did not prevents Dbs binding. The activation of Cdc42 and consequently formation of filopodia in response to upstream signals is mediated by guanine nucleotide exchange factors (GEFs), which accelerates GDP dissociation from Cdc:GDP inactive complex and this way stimulates formation of the GTP-bound active form of Cdc42. For this reason if the MLS000693334 binds/or competes with GEF, there should be inhibition of GDP/GTP exchange and as a result we will observe inhibition of filopodia formation. For this reason we asked whether Cdc42 specific inhibitor would be able to change GEF activity. We incubated [3H]GDP: Cdc42 wt DMSO or MLS000693334 and then initiated exchange reaction with guanine nucleotide exchange factor (Dbs) in the presence of GTP.

FIG. 7 B shows western blot analysis with phospho-specific p38 antibody revealed that Cdc42 inhibitor is not preventing p38 phosphorylation induced by activation of RBL cells by two different pathways FIG. 7 C shows that SB 202190, a highly selective, cell—permeable inhibitor of p38 MAP kinase, has a similar structure as Cdc42 specific MLS000693334 and MLS000682339.

FIG. 7 D shows the results that p38 specific inhibitor, SB 202190, did not inhibit fluorescent—GTP binding to Cdc42.

Figure 8:
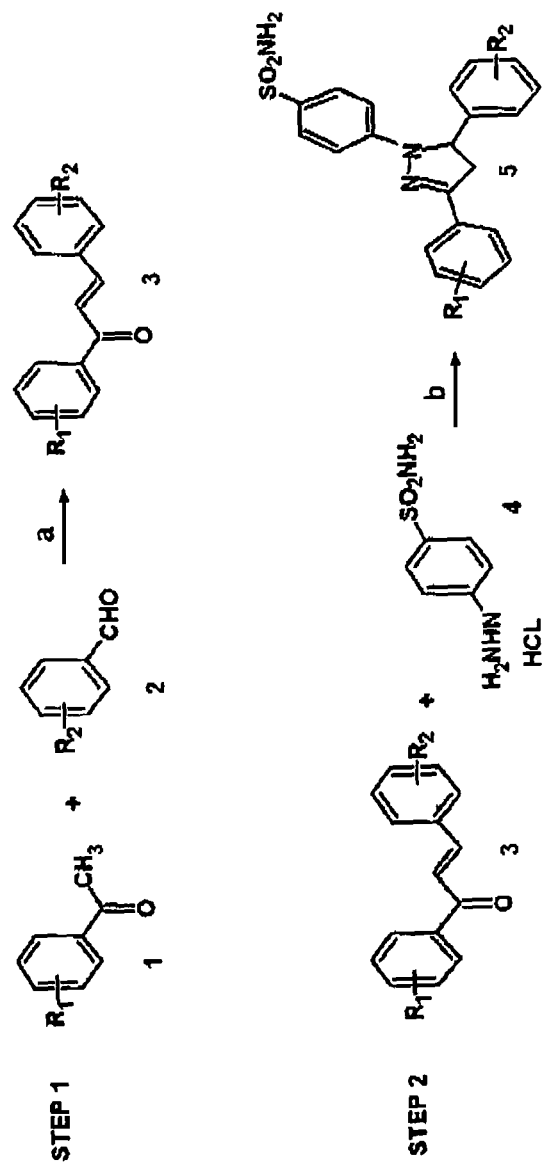

FIG. 8 provides a general synthetic route to the dihydropyrazolines of the present invention. The reagents for the individual reactions are as follows: (a) NaOH, EtOH, $H_2O$, 0° C. to rt, 12 h-36 h; (b) microwave, with or without AcOH, 120-160° C., 1-2 h.

Figure 9:
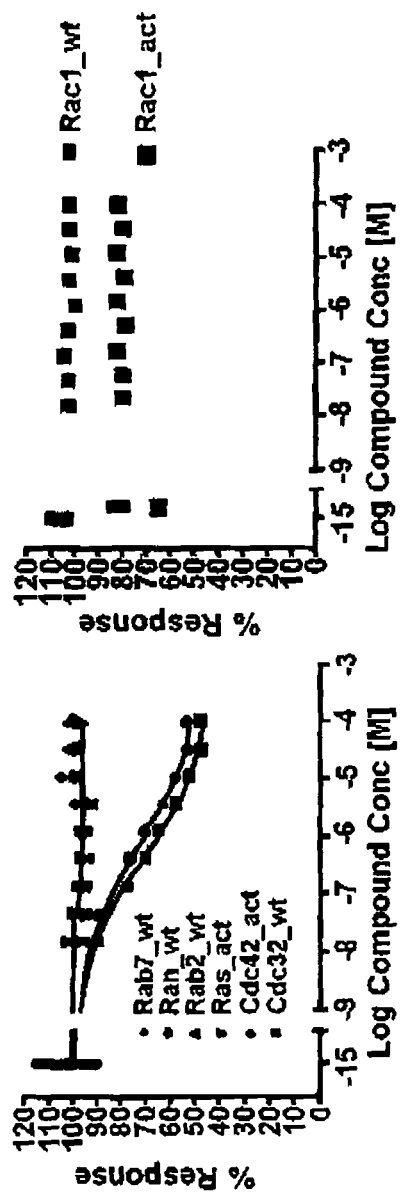

FIG. 9 shows the primary dose response assay date for CID 44216842 set forth in the figure.

FIG. 10 shows six preferred compounds according to the present invention and their CID numbers. Data generated for these compounds in a GLISA assay indicated that compound CID 44143700 and 13927310 shows significant response at approximately 10 μM to inhibit Cdc42 GTPase with similar potency and efficacy to each others.

DETAILED DESCRIPTION OF THE INVENTION

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal (i.e., not a laboratory test animal) and preferably a human, to whom treatment, including prophylactic treatment (prophylaxis), with the compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers, individual optical isomers or racemic mixtures and/or diastereomers (in context), pharmaceutically acceptable salts and prodrug forms. Within its use in context, the term compound may refer to a single compound or a mixture of compounds as otherwise described herein.

The term "bioactive agent" refers to any biologically active compound or drug which may be formulated for use in the present invention. Exemplary bioactive agents include the compounds according to the present invention which are used to modulate Cdc42 GTPase and to treat cancer, other genetic and acquired disease states as well as infections caused by microbes and fungi as well as other compounds or agents which are otherwise described herein.

The terms "treat", "treating", and "treatment", are used synonymously to refer to any action providing a benefit to a patient at risk for or afflicted with a disease, including improvement in the condition through lessening or suppression of at least one symptom, delay in progression of the disease, prevention or delay in the onset of the disease, etc. Treatment, as used herein, encompasses both prophylactic and therapeutic treatment. Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease that subsequently occurs. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate an infection as otherwise described herein; in another embodiment, administration of the compounds according to the present invention is effective to decrease the severity of the disease or lengthen the lifespan of the mammal so afflicted, in the case of cancer, as well as other diseases that are Cdc42 GTPase driven, including for example, Huntington's disease, Parkinson's disease, Alzheimer's disease, amyotrophic lateral sclerosis (ALS or Lou Gehrig's disease), rheumatoid arthritis, atherosclerosis, diabetes type I, autosomal dominant polycystic kidney disease, cystic kidney disease and precystic kidney disease, among others, including various microbial and other infections as otherwise described herein.

The term "pharmaceutically acceptable" as used herein means that the compound or composition is suitable for administration to a subject to achieve the treatments described herein, without unduly deleterious side effects in light of the severity of the disease and necessity of the treatment.

The term "inhibit" as used herein refers to the partial or complete elimination of a potential effect, while inhibitors are compounds that have the ability to inhibit.

The term "prevention" when used in context shall mean "reducing the likelihood" or preventing a condition or disease state from occurring as a consequence of administration or concurrent administration of one or more compounds or compositions according to the present invention, alone or in combination with another agent. It is noted that prophylaxis will rarely be 100% effective; consequently the terms prevention and reducing the likelihood are used to denote the fact that within a given population of patients of subjects, administration with compounds according to the present invention will reduce the likelihood or inhibit a particular condition or disease state (in particular, the worsening of a disease state such as the metastasis of cancer or other accepted indicators of disease progression in the case of inflammatory and neurologic diseases) from occurring.

The term "cancer" shall refer to a proliferation of tumor cells having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. The term cancer also within context, includes drug resistant cancers, including multiple drug resistant cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas, among others. It is noted that certain cancers and tumors including especially B-cell lymphoma, stomach cancer including gastric adenocarcinoma, leukemias, including myeloid and B-cell leukemias, breast, cervical, ovarian, testicular and prostate cancer among others which exhibit high levels of Cdc42 GTPase expression are principal target cancers for compounds and therapies according to the present invention.

The term "additional anti-cancer agent" is used to describe an additional compound which may be coadministered with one or more compounds of the present invention in the treatment of cancer. Such agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258,); 3-[5-(methylsulfonylpiperadinemethyl)-indolyl]-quinolone, vatalanib, AG-013736, AVE-0005, the acetate salt of [D-Ser(But) 6, Azgly 10] (pyro-Glu-His-Trp-Ser-Tyr-D-Ser(But)-Leu-Arg-Pro-Azgly-NH$_2$ acetate [$C_{59}H_{84}N_{18}O_{14}$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mercaptopurine, deoxycoformycin, calcitriol, vairubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

The term "alkyl" is used herein to refer to a fully saturated monovalent radical containing carbon and hydrogen (up to 20 carbon atoms or as otherwise indicated), and which may be a straight chain, branched or cyclic. Examples of alkyl groups are methyl, ethyl, n-butyl, n-heptyl, isopropyl, 2-methyl propyl, tert-butyl, neopentyl, etc.

The term "substituted" as that term relates to alkyl groups which are described above include one or more functional groups such as lower alkyl groups containing 1-6 carbon atoms, aryl (especially, phenyl or naphthyl, preferably phenyl), substituted aryl (as described below), acyl ($C_1$-$C_{10}$, preferably, $C_2$-$C_6$), halogen (F, Cl, Br, I, e.g., alkyl halos, e.g., $CF_3$), amido, thioamido, cyano, nitro, alkynyl ($C_2$-$C_6$), azido, hydroxy, alkoxy ($C_1$-$C_6$), amino, $C_1$-$C_6$ alkyl and dialkyl-amino, $C_2$-$C_6$ acylamino, $C_2$-$C_6$ oxyester or carboxyester, aryloxy, aryloxy($C_1$-$C_6$)alkyl, carboxamido, thio, $C_2$-$C_6$ ether or thioether and the like.

The term "aryl", when used in context, refers to a substituted or unsubstituted monovalent aromatic radical having a single ring (e.g., phenyl) or multiple ring (naphthyl). Other examples include heterocyclic aromatic (heteroaromatic or heteroaryl) ring groups having one or more nitrogen, oxygen, or sulfur atoms in the ring, such as the 5 or 6-membered heteroaryls oxazolyl, isoxazolyl, pyrazolyl, thiazolyl, thiadiazolyl, triazolyl, tetrazolyl, imidazolyl, furyl, pyrrolyl, pyridyl, thienyl, pyridazinyl, pyrimidyl, among others.

The term "substituted" as used in the term "substituted aryl, substituted aromatic, substituted heteroaryl, or substituted heteroaromatic" herein signifies that one or more substituents (1, 2, 3 or 4, preferably 1 or 2) may be present, said substituents being selected from atoms and groups, which when present do not prevent the compound from functioning as an inhibitor of Cdc42 GTPase. Examples of substituents that may be present in a substituted aromatic or heteroaromatic group include, but are not limited to, groups such as ($C_1$-$C_6$) alkyl, ($C_1$-$C_{10}$, preferably, $C_2$-$C_6$) acyl, aryl, heteroaryl (described above), substituted aryl and heteroaryl, halogen, cyano, nitro, amido (optionally substituted with one or two $C_1$-$C_6$ alkyl groups), thioamido (optionally substituted with one or two $C_1$-$C_6$ alkyl groups), azido, alkynyl ($C_2$-$C_6$), ($C_1$-$C_6$) alkylhalos (e.g., $CF_3$), hydroxy, ($C_1$-$C_6$) alkoxy, ($C_2$-$C_8$) alkoxyalkyl, amino, ($C_1$-$C_6$) alkyl and dialkyl amino, ($C_1$-$C_6$) acylamino, ($C_1$-$C_6$) acyloxy, aryloxy, ($C_1$-$C_6$) aryloxyalkyl, ($C_1$-$C_6$) carboxyalkyl, carboxamido, thio, ($C_1$-$C_6$) thioethers, both saturated and unsaturated ($C_3$-$C_8$) cyclic hydrocarbons, ($C_3$-$C_8$) heterocycles and the like. It is noted that each of the substituents disclosed herein may themselves be substituted.

The term "heteroaryl", a subset of aryl, refers to an unsaturated carbocylic ring wherein one or more carbon atoms have been replaced with one or more heteroatoms such as nitrogen, oxygen or sulfur. Examples of heteroaryls is described above. "5-membered heteroaryl" refers to heteroaryls containing 5 atoms within the heteroaryl ring. "6-ring heteroaryls" refers to heteroaryls containing 6 atoms within the heteroaryl ring. Heteroaryls may be unsubstituted or substituted as otherwise described herein. Exemplary 5 or 6-membered heteroaryls include, for example, oxazolyl, isoxazolyl, pyrazolyl, thiazolyl, thiadiazolyl, triazolyl, tetrazolyl, imidazolyl, furyl, pyrrolyl, pyridyl, thienyl, pyridazinyl, pyrimidyl The term "heterocyclic" refers to a ring system containing from 3 to 8 atoms from 1 to 4 of which atoms are nitrogen, oxygen, or sulfur. 5- or 6-membered heterocycles, when used, are preferred. Heterocycles may be saturated or unsaturated, depending upon the context of use. When unsaturated heterocycles are also referred to as heteroaryls, when fully saturated, they are referred to as heterocycles.

The term "GTPase" is used to describe the Rho family of GTPases, which is a family of small signaling GTPases, of which Cdc42 is most relevant in this application. Cdc42 GTPase has utility in the treatment of a number of diseases, as well as cancers and microbial/fungal infections, etc. as described herein. Cdc42 is a GTPase protein involved in regulation of the cell cycle, cell differentiation and cell migration.

The term "co-administration" or "adjunct therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time. The term co-administration or adjunct therapy also contemplates other bioactive agents being coadministered with pharmaceutical compositions according to the present invention, especially where a cancer has metastasized or is at risk for metastasis.

Compounds according to the present invention may be readily formulated into pharmaceutical compositions, useful in the treatment of disease states and conditions and infections as otherwise described hereinabove. Pharmaceutical compositions comprise an effective amount of one or more compounds according to the present invention in combination with a pharmaceutically acceptable carrier, additive or excipient, optionally in combination with at least one additional anticancer agent or other agent effective for the purpose for which the composition is intended. In addition to anticancer agents, the present invention also contemplates the coadministration of an antimicrobial or antifungal agent, depending upon the final use for which the pharmaceutical composition is intended. Typical antimicrobial agents/antibiotics include the aminoglycosides, ansamycins, carbacephems, carbapenems, cephalosporins, glycopeptides, lincosamides, lipopeptides, macrolides, monobacftams, nitrofurans, penicillins, polypeptides, quinolones, sulfonamides, tetracyclines and anti-mycoacterials, among others. Typical antifungal agents include the polyenes, imidazoles, triazoles, thiazoles, allylamines and echinocandins, among others.

The present invention includes the compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

As noted above, the compounds and methods of the invention modulate (generally through inhibition) Cdc42 GTPase as otherwise described herein, and are useful for the inhibition (including prophylaxis) and/or treatment of cancer as described herein above, a number of disease states and/or conditions, including Alzheimer's disease, Huntington's disease, Parkinson's disease, amyotrophic lateral sclerosis (ALS or Lou Gehrig's disease), rheumatoid arthritis, atherosclerosis, diabetes type I, autosomal dominant polycystic kidney disease, cystic kidney disease, precystic kidney disease, microbial infections, including *Chlamydia* infections, *E. coli* infections, *H. pylori* infections and its secondary effects including gastric ulcers, *Coxiella Brunetti* (Q-fever) infections and *Streptococcus pneumonia* infections, fungal infections including *Paracoccidiodes brasiliensis* and *Candida albicans* and their secondary effects including lung edema. Additionally, compounds according to the present invention may be used to inhibit rejection (graft host response) in transplant patients (pursuant to transplantation), to promote immunosuppression, anti-inflammatory response and to mobilize stem cell (migration) in patients in need.

In methods according to the present invention, subjects or patients in need are treated with the present compounds, pharmaceutical compositions in order to inhibit, reduce the likelihood or treat a disease state, condition and/or infection as otherwise described herein. The disease states, conditions and infections treated by the present compounds and compositions are readily recognized and diagnosed by those of ordinary skill in the art and treated by administering to the patient an effective amount of one or more compounds according to the present invention.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical additives, carriers and excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or are apparent to those skilled in the art; for example, see Remington's Pharmaceutical Sciences (17th Ed., Mack Pub. Co., 1985). The composition to be administered will contain a quantity of the selected compound in a pharmaceutically effective amount for modulating GTPase in a subject according to the present invention in a subject.

Synthesis of Compounds According to the Present Invention

The compounds according to the present invention are readily known in the art and their synthesis is well-known and readily provided. Most of the compounds are known in the art and can be found in published literature, purchased from commercial sources or readily prepared from starting materials which are readily obtained from commercial sources. Substituted phenyl or naphthyl compounds, principally used in the present invention are well known in the art. The various substituents may be readily introduced into the pyrazoline (dihydropyrazole) pharmacophore to produce dihydropyrazolines according to the present invention. Introduction of aryl groups onto the various positions of the dihydropyrazole pharmacophore follows standing chemical synthetic approaches well known in the art, adapted to accommodate the varying chemistries associated therewith. Synthesis of all of the presently described compounds are well within the routineer's skill in the art, inasmuch as the reactions to produce the final compounds are rather facile and can generally be performed, with relatively few exceptions, in two or three simple steps, using readily (commercially or from the literature) available intermediates in two or three simple steps. Substitution of alternative optionally substituted heteroaryl groups for the phenyl groups presented in the scheme are generally routine. Many of these substituted heteroaryls are commercially available or readily prepared from literature syntheses, either directly or by analogy.

By way of example, FIG. 8 provides a general scheme for the chemical synthesis of dihydropyrazolines according to the present invention. In particular, pursuant to the chemical scheme, an appropriately substituted acetophenone derivative (1, labeled in the attached FIG. 8 with substituent $R_1$) is reacted with (condensed) a substituted benzaldehyde compound (2) to produce the appropriately labeled chalcone (3). In a second step of the synthesis, the substituted chalcone which is produced in step 1, is reacted with an appropriately substituted phenyl hydrazine compound (4) to produce the aryl substituted dihydropyrazole compound (5).

Method of Treatment

According to one aspect of the invention, a method is provided for treating a mammalian patient or subject to modulate GTPase, in particular the Rho family of GTPases including Cdc42. Agonist and/or antagonist activity of compounds according to the present invention described herein may be used to modulate GTPase in a manner consistent with inhibiting and/or treating disease states and/or conditions such as cancers, including metastatic cancer (e.g., especially B-cell lymphoma, stomach cancer including gastric adenocarcinoma, leukemias, including myeloid and B-cell leukemias, breast, cervical, ovarian, testicular and prostate cancer, among others where Cdc42 GTPase is overexpressed or hyperactivated), genetic and acquired diseases where activation of Cdc42 GTPase plays a pivotal role (e.g., neurodegenerative diseases, including Alzheimer's disease, Huntington's disease, Parkinson's disease, amyotrophic lateral sclerosis (ALS or Lou Gehrig's disease), rheumatoid arthritis, atherosclerosis, diabetes type I, autosomal dominant polycystic kidney disease, cystic kidney disease, precystic kidney disease, microbial infections, including *Chlamydia* infections, *E. coli* infections, *H. pylori* infections and its secondary effects including gastric ulcers, *Coxiella Brunetti* (Q-fever) infections and *Streptococcus pneumonia* infections, fungal infections including *Paracoccidiodes brasiliensis* and *Candida albicans* and their secondary effects including lung edema. Additionally, compounds according to the present invention may be used to inhibit rejection (graft host response) in transplant patients (pursuant to transplantation), to promote immunosuppression, anti-inflammatory response and to mobilize stem cell (migration) in patients in need, among others. Antagonist activity associated with Cdc42 GTPase inhibition is a particularly useful aspect of the present invention.

According to the present invention, in patients or subjects in need thereof, are treated by administering to the patient or subject an effective amount of one or more compounds according to the present invention, optionally in combination with at least one additional bioactive agent useful for treating the same disease state or condition. Compounds according to the present invention may be used to inhibit, reduce the likelihood or treat cancer, including the metastasis of cancer in a patient or subject in need of such treatment. The treatment is useful for any cancer which is mediated by Cdc42 GTPase or for which metastasis is a risk element. Therapy with at least one additional anticancer agent as otherwise described herein is also contemplated in the present methods. The numerous cancers which may be treated pursuant to the present method are described hereinabove.

In another aspect the present invention is directed to a method for treating a genetic or acquired disease in which activation of Cdc42 GTPase plays a significant role. These disease states and/or conditions include, for example rheumatoid arthritis, atherosclerosis, diabetes (type I), Huntington's disease, Alzheimer's disease, Parkinson's disease, amyotrophic lateral sclerosis (ALS or Lou Gehrig's disease), rheumatoid arthritis, atherosclerosis, diabetes type I, autosomal dominant polycystic kidney disease, cystic kidney disease, and precystic kidney disease. In this method, a patient or subject in need of treatment is administered an effective amount of a compound as otherwise described herein optionally in combination with a pharmaceutically acceptable carrier, additive or excipient.

In another aspect, the invention provides a method for reducing, inhibiting and/or treating infections, disease states or conditions which are caused by *Chlamydia, E. coli, H. pylori* and its secondary effects including gastric ulcers, *Coxiella Brunetti* (Q-fever), *Streptococcus pneumonia*, and fungi including *Paracoccidiodes brasiliensis* and *Candida albicans* and their secondary effects including lung edema. Additionally, compounds according to the present invention may be used to inhibit rejection (graft host response) in transplant patients (pursuant to transplantation), to promote immunosuppression, anti-inflammatory response and to mobilize stem cell (migration) in patients in need, among others.

The disease states and/or conditions are treated using compounds according to the present invention. In this aspect, the method of the present invention comprises administering to a subject or patient in need an amount of a compound of the invention, the amount being sufficient to reduce, inhibit or cure infection and/or a disease state and/or condition caused by *Chlamydia, E. coli, H. pylori* and its secondary effects including gastric ulcers, *Coxiella Brunetti* (Q-fever), *Streptococcus pneumonia*, and fungi including *Paracoccidiodes brasiliensis* and *Candida albicans*. The compounds according to the present invention may be used alone or combined with another agent useful in treating infections including any one or more of the traditional antibiotics and/or antifungal agents or as otherwise described herein.

In the present invention, the method of treatment comprises administering to the subject in need of treatment, in a pharmaceutically acceptable carrier, an effective amount of a compound according to I below:

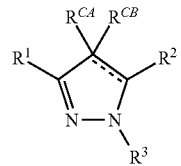

I

Wherein $R^1$ and $R^2$ are each independently an optionally substituted aryl group, preferably a phenyl group which is optionally substituted;
$R^3$ is a phenyl group which is substituted with an ortho, meta or para sulfonamide group (preferably, a para sulfonamide group) according to the chemical structure

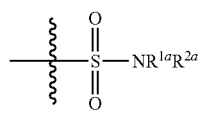

Where $R^{1a}$ and $R^{2a}$ are each independently H or a $C_1$-$C_4$ alkyl group (preferably H or methyl, more preferably H) which may be optionally substituted with a hydroxyl group, wherein $R^3$ may be further optionally substituted;
$R^{CA}$ is H or a $C_1$-$C_4$ alkyl group which is optionally substituted with a hydroxyl group; and
$R^{CB}$ is absent H or a $C_1$-$C_4$ alkyl group which is optionally substituted with a hydroxyl group (preferably, both $R^{CA}$ and $R^{CB}$ are H),
Or a pharmaceutically acceptable salt, enantiomer, diastereomer, solvate or polymorph thereof.

In certain preferred aspects of the invention, the compound used is according to the chemical structure

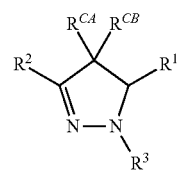

II

Where $R^1$ and $R^2$ are the same as described above;
$R^3$ is a phenyl group which is substituted with a para-sulfonamide group

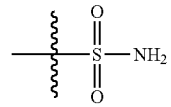 [SMILES: *S(N)(=O)=O]

and may be further optionally substituted; and
$R^{CA}$ and $R^{CB}$ are both H, or
a pharmaceutically accept salt, enantiomer, solvate or polymorph thereof.

In still additional aspects of the invention, the compound used in the method is according to the chemical structure:

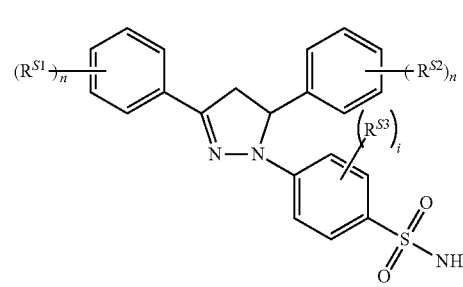

III

Where $R^{S1}$, $R^{S2}$ an $R^{S3}$ are each independently H, an optionally substituted $C_1$-$C_{10}$ (preferably, $C_1$-$C_6$) alkyl group (preferably methyl or isopropyl), a halogen (F, Cl, Br, I, preferably F), hydroxyl, a cyano group, a nitro group, an optionally substituted acyl ($C_1$-$C_{10}$) an optionally substituted $C_1$-$C_{10}$ (preferably $C_1$-$C_6$) alkoxy group, an optionally substituted $C_2$-$C_{10}$ ester (oxycarbonyl ester or carbonyloxyester) group, an optionally substituted $C_2$-$C_{10}$ ether group, an optionally substituted $C_2$-$C_{10}$ alkoxyether group, a carboxamido group (optionally substituted with one or two $C_1$-$C_6$ alkyl groups), aminocarbonyl (optionally substituted with a $C_1$-$C_6$ alkyl group), thioamido (optionally substituted with one or two $C_1$-$C_6$ alkyl groups), azido, $C_2$-$C_{10}$ (preferably $C_2$-$C_6$) alkenyl or alkynyl (preferably alkynyl), amino, ($C_1$-$C_6$) alkyl and dialkyl amino, aryloxy, thio, ($C_1$-$C_6$) thioether or a ($C_3$-$C_9$) monocyclic or bicyclic heterocyclic group, among others; n is 0, 1, 2 or 3 and i is 0, 1 or 2, or a pharmaceutically accept salt, enantiomer, solvate or polymorph thereof.

In additional preferred aspects of the invention, in the compounds according to chemical structure III used in the method aspects, $R^{S1}$ and $R^{S2}$ are independently H, halogen (preferably, Br or Cl, more preferably Br), a $C_1$-$C_4$ alkyl group (preferably methyl) or a $C_1$-$C_6$ alkoxy (preferably methoxy) group, $R^{S3}$ is H and n is 0 or 1 and i is 0.

Additional preferred compounds which are used in method aspects of the present invention include the following compounds or their pharmaceutically acceptable salts, enantiomers, solvates or polymorphs thereof:

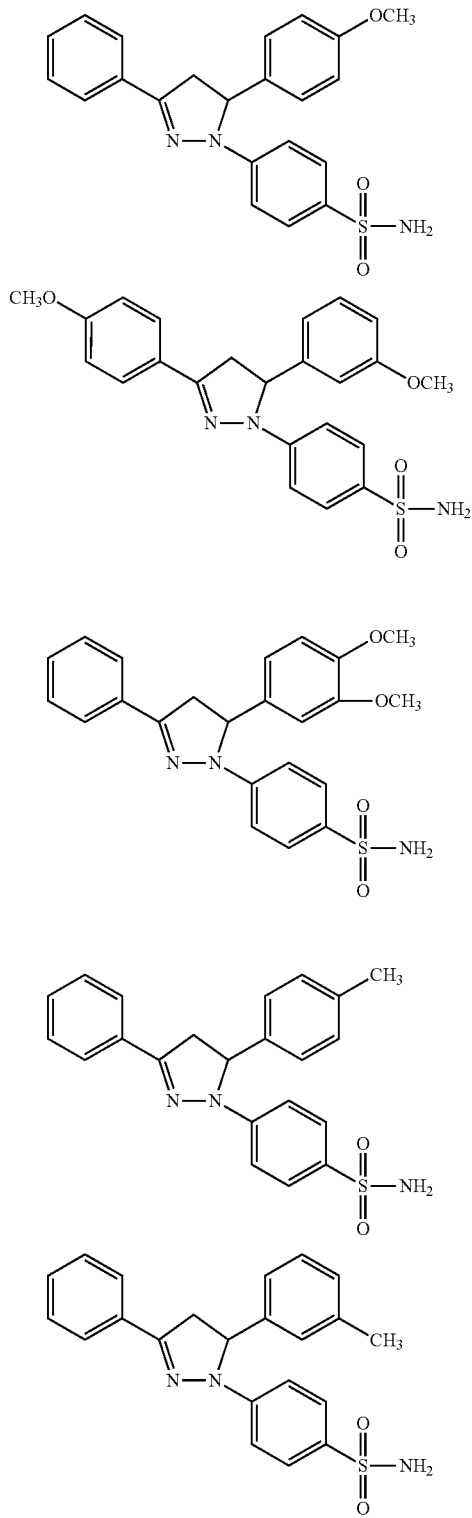

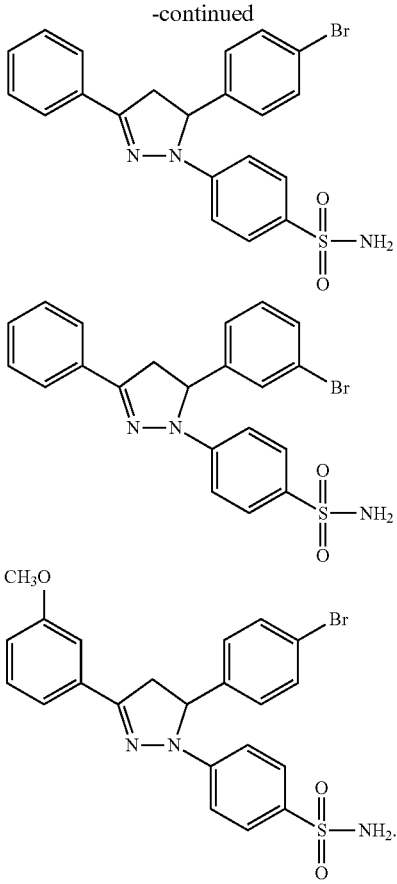

In the methods of treating or inhibiting cancer or the metastasis of cancer, the compounds described above may be coadministered with at least one additional anticancer agent including, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(But)6,Azgly 10] (pyro-Glu-His-Trp-Ser-Tyr-D-Ser(But)-Leu-Arg-Pro-Azgly-$NH_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others, and mixtures thereof.

In methods involving infections, disease states and/or conditions caused by *Chlamydia, E. coli, H. pylori* and its secondary effects including gastric ulcers, *Coxiella Brunetti* (Q-fever) and *Streptococcus pneumonia*, fungi infections including *Paracoccidiodes brasiliensis* and *Candida albicans* and their secondary effects including lung edema, at least one compound according to the present invention, alone or in combination with at least one further agent selected from the group consisting of antibiotics and/or antifungal agents as otherwise described herein is administered in an effective amount to a patient of subject in need thereof.

In still further method aspects of the invention, compounds according to the present invention may be used to inhibit rejection (graft host response) in transplant patients (pursuant to transplantation), to promote immunosuppression, anti-inflammatory response and to mobilize stem cell (migration) in patients in need, among others.

The following examples illustrate but are not intended in any way to limit the invention.

Experimental Rationale and Approach

The Ras-homologous (Rho) family GTPases and their effector proteins are major regulators of signaling pathways that control diverse biological processes. The most extensively characterized Rho-family members are RhoA, Rac1 and Cdc42 {Jaffe and Hall, 2005, Annu Rev Cell Dev Biol, 21, 247-69}. Actin cytoskeleton reorganization is a well-characterized function of Rho GTPases with Rac1 regulating lamellipodia, Cdc42 regulating filopodia and RhoA regulating stress fiber formation {Bishop, 2000}. Rho-family GTPases also regulate cell-cycle progression, cell growth and survival, gene transcription, adhesion, migration, phagocytosis and cytokinesis as well as neurite extension and retraction, cellular morphogenesis and polarization {Chimini, 2000; Etienne-Manneville, 2002; Raftopoulou, 2004}. Consequently, the activity of Rho GTPases must be tightly controlled through selective activation and localization.

Rho GTPases are coupled to receptor signaling and as a result are responsive to external cues. Growth factor signaling triggers conversion from the inactive/GDP-bound to the active/GTP-bound states {Jaffe, 2005}. Activation and inactivation are controlled by Rho-family specific regulatory proteins that regulate membrane translocation and nucleotide bound status. In resting cells, Rho-family GTPases exist predominantly in the inactive GDP-bound form in associated with Rho GDP-dissociation-inhibitor (GDI) {Johnson et al., 2009, J Biol Chem, 284, 23860-71}. By binding to the C-terminus of Rho-family GTPases, Rho-GDI prevents the GTPases from binding to the plasma membranes and retains them in the cytoplasm {Johnson, 2009; Ridley, 2006}. In response to growth factors and activation of tyrosine kinases or G-protein coupled receptor activation, Rho-family guanine nucleotide exchange factors (GEFs) promote conversion to the GTP-bound state and activate the respective target GTPases at the plasma membrane where they actively promote localized actin remodeling for cell migration and differentiation. Termination of signaling promotes return of the GTPases to the resting state through the action of GTPase-activating protein stimulated hydrolysis of GTP and sequestration by GDI {Rossman, 2005; Bos, 2007}.

Because of key functions of Rho family GTPases in cell migration and differentiation, their aberrant regulation or expression is closely linked to tumorigenesis and disease pathogenesis (reviewed in {Takai, 2001; Rossman, 2005; Van Hennik, 2005; Boettner, 2002; Gomez del Pulgar, 2005; Sahai, 2002; Vega, 2008}). Identifying small, cell permeable molecules that selectively and reversibly regulate Rho GTPases is therefore of high scientific and potentially therapeutic interest. Inhibitors that specifically interact with Rho family GTPases are limited. Thus far, two low molecular weight inhibitors for Rac1 have been described {Gao, 2004; Shutes, 2007}. NSC23766 is cell-permeable and directly binds a groove of Rac1 that is critical for GEF interaction. Therefore, NSC23766 blocks Rac activation by some, but not other, GEFs that activate Rac1 {Gao, 2004}. More promising is the Rac-specific inhibitor EHT1864, which binds tightly to Rac1, Rac1b, Rac2 and Rac3, reduces their affinity for GTP. EHT1864 induces nucleotide release and inhibits nucleotide rebinding. Because all Rac effector interactions are GTP-dependent, EHT1864 is expected to block Rac1 interaction with all effectors {Shutes, 2007}. The only known small molecule inhibitor of Cdc42 activation, secramine, inhibits Cdc42 activation only in its prenylated form. Activation of the non-prenylated form of the Cdc42, which does not bind GDI, was unaffected by the inhibitor indicating that secramine inhibits activation of Cdc42 in a Rho GDI-dependent manner. This was supported by the finding that secramine prevents translocation of prenylated Cdc42 to membranes {Pelish, 2006}. Thus, there is a need to systematically identify further inhibitors.

To identify and characterize selective probes for Ras-like GTPases, we undertook a high throughput screen using a library of nearly 200,000 compounds from the Molecular Libraries Screening Center Network (http://nihroadmap.nih.gov/molecularlibraries/). The screen was based on a highly sensitive flow cytometric, fluorescent GTP-binding assay that allows real-time measurement and therefore identified both activators and inhibitors of GTP-binding. In addition, the unique multiplexing capabilities of flow cytometry[33-35] enabled the simultaneous, quantitative analysis of the activation or inhibition of up to eight GTPases immobilized on color-coded microspheres by small molecules, providing an unprecedented opportunity to both evaluate selectivity towards diverse family members and structure activity relationships. Here we focus on the analysis of a compound that was identified as an allosteric inhibitor of GTP-binding by Cdc42 and report structure activity relationships based on synthesis of chemical derivatives.

Experimental Procedures
Multiplexed Primary Screens

Figures 1A, 1B:
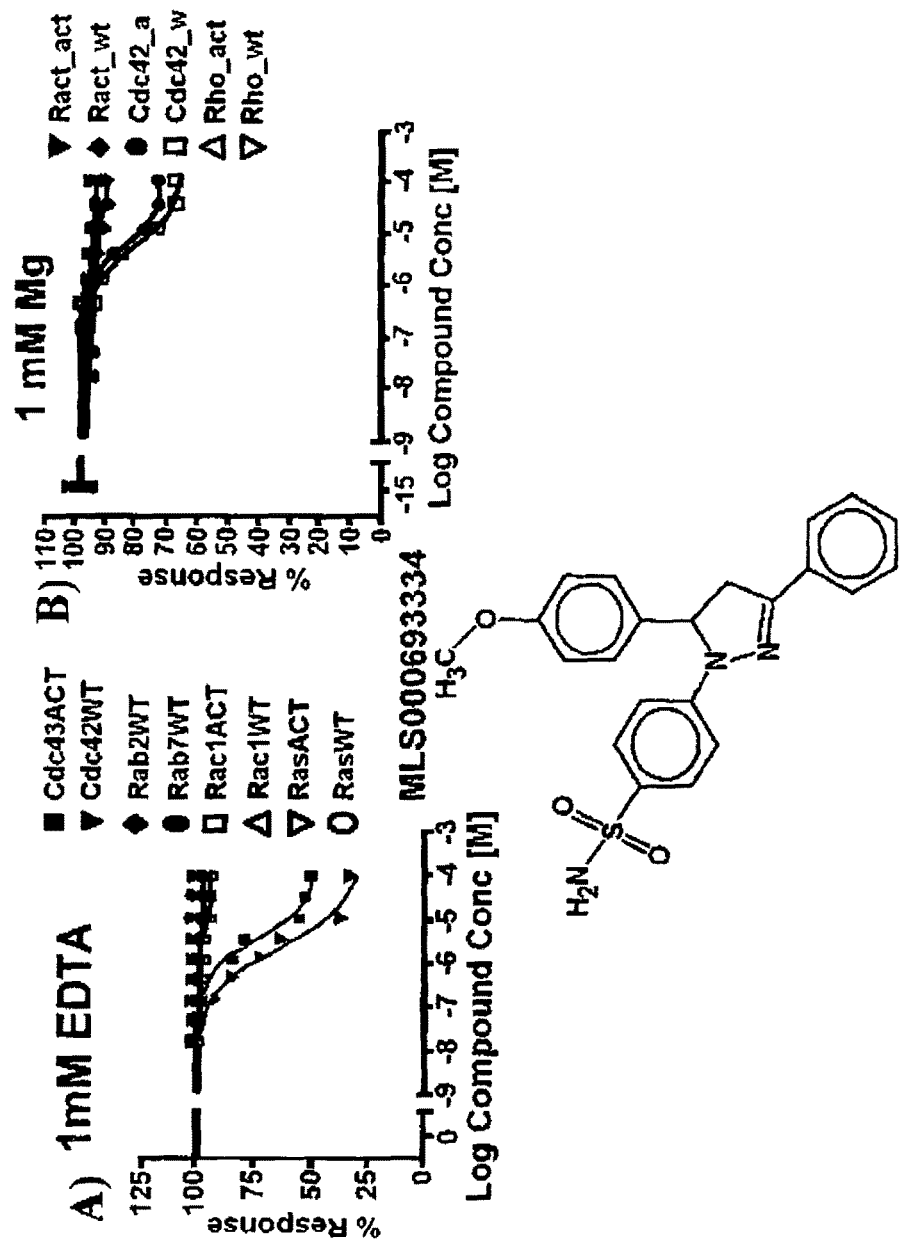
FIG. 1 A shows that MLS000693334 was a specific inhibitor for Cdc42 wt and Cdc42(Q61L) in the presence of Mg ions ($EC_{50} \sim 4 \times 10^{-6}$ M) and did not affect activity of other Rho family GTPases. Thus, using flow cytometry measurements for multiplex, high throughput screening we identified novel inhibitor for the Rho-family GTPase Cdc42.

Multiplex screening was performed by measuring GTP-binding activities of six GTPases (Cdc42, Rab2, Rab7, activated Rac1Q61L, Rac1, and H-Ras) simultaneously using special glutathione (GSH) bead sets having varied fluorescence intensities at a fixed wavelength[38]. Individual GST-GTPase chimeras were tested against approximately 200,000 small molecules from the Molecular Libraries Small Molecule Repository (MLSMR). Results of fluorescent GTP-binding from the entire primary screen are summarized in the open access Pubchem database as required for projects conducted under the Roadmap Initiative (AID 757-761, 764). FIG. 1 illustrates the HTS assay and shows the time-dependent data from one 384-well plate with a single activator (compound identification number-CID888706) out of 320 test compounds on the plate. In total 1877 compounds/194,635 were identified as activators or inhibitors in the primary screen. On the order of 100-500 compounds were found active per GTPase target, enabling an unprecedented comprehensive evaluation of small molecules active against various Ras-related GTPase family members. Here we report one compound active specifically on Cdc42 and structure activity relationships determined through chemical synthesis.

Multiplex analysis of small GTPases, were performed as we have described previously {Surviladze, 2009}. Briefly, six individual GST-GTPases (H-Ras wt, Cdc42 wt, Rac1 wt and Racq61L mutant were purchased from Cytoskeleton, and GST-Rab2, GST-Rab7 were purified as described. {Schwartz, 2008 #34}) were attached to 4 μm diameter glutathione-beads (GSH-beads) distinguished by different intensities of red color (various magnitude of emission at 665+/−10 nm with excitation at 635 nm). Bead sets for multiplex assays were custom synthesized by Duke Scientific Corp (Fremont, Calif.), but may now be ordered from Thermo/Fisher. Individual GTPase-coupled beads were washed twice with 100 μl ice cold NP-HPS buffer [(0.01% (vol/vol) NP-40, 30 mM HEPES pH 7.5, 100 mM KCl, 20 mM NaCl,] supplemented with 1 mM EDTA, 0.1% BSA and 1 mM DTT and were pooled together immediately prior to loading of 5 μl of this mixture in each well of the assay plates. Next 0.1 μl of test compounds (1 mM stock in DMSO) were added to individual wells to give a final concentration of 10 μM compound and 1% DMSO, after which 5 μl BODIPY-FL-GTP (200 nM stock in NP-HPSE) was added to each well. Positive controls, contained the bead mixture, 0.1 μl DMSO (1% final) and fluorescent GTP. Negative controls, contained the bead mixture with fluorescent GTP, 0.5 mM unlabeled GTP as a competitor, and 1% DMSO. Plates were incubated on rotator for 40-45 min at 4° C. and sample analysis was conducted with a HyperCyt® high throughput flow cytometry platform as described previously {Kuckuck, 2001 #51}. Flow cytometric light scatter and fluorescence emission at 530+/−20 nm (FL1) and 665+/−10 nm (FL8) were collected on a Cyan ADP flow cytometer (Beckman Coulter, Fullerton, Calif.). The resulting time-dependent data (one file per plate) were analyzed using IDLQuery software to determine the compound activity in each well. Gating based on forward scatter (FS) and side scatter (SS) parameters was used to identify singlet bead populations. Gating based on FL8 emission distinguishes the beads coated with different proteins, and the median fluorescence per bead population was calculated. A compound was considered a "potential active" if the change in activity was greater than 20% from baseline. Baselines were set to 100% based on measurements from the 1% DMSO containing positive controls as further described in PubChem. {PubChem #72}

Dose Response Measurements

Figures 1D, 1E:
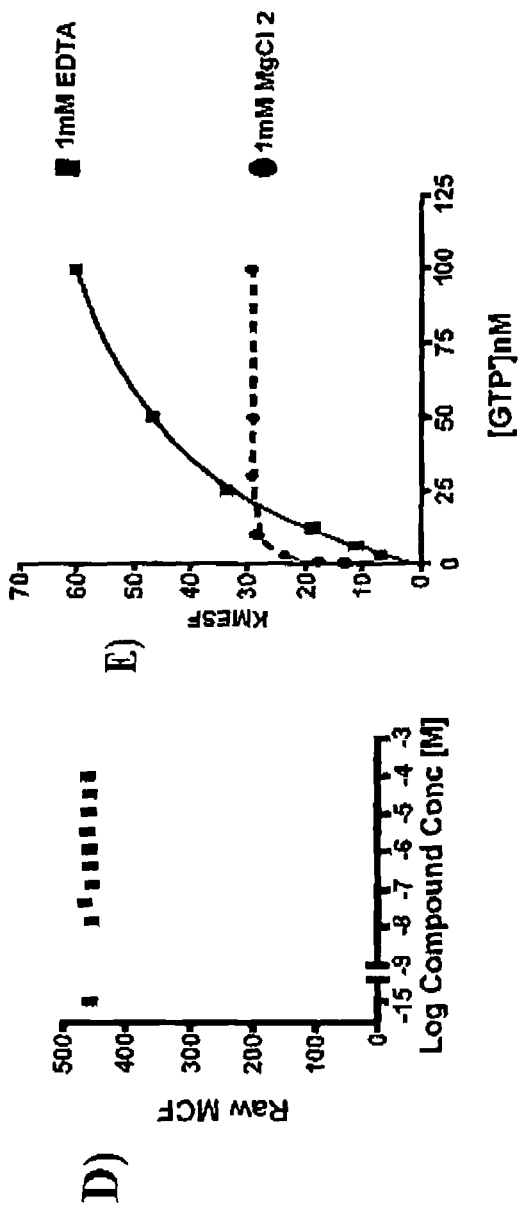

Dose Response Measurements has been previously described {Surviladze, 2009 #48}. Briefly, compounds were serially diluted 1:3 a total of eight times from a starting concentration of 10 mM giving a 9-point dilution series in DMSO. The final concentrations of inhibitors in the assay ranged from 10 nM to 100 μM. Dose-response analyses were examined in the presence of NP-HPS buffer containing: a) 1 mM EDTA; or b) 1 mM $MgCl_2$. (FIGS. 1D and E). For assays with EDTA we used one multiplex (Rab7 wt, Rab2 wt, H-Ras wt, H-RasG12V, Cdc42 wt, and Cdc42Q61L) and 3 single-plexes (for Rac1 wt, Rac1 Q61L and GST-GFP). In total 1243 compounds were tested in dose response assays based on both MLSMR and ChemDiv virtual screening.

Changes in GTP binding affinity ($K_d$) and $B_{max}$ in the presence of a given compound were measured in multiplex (Cdc42, Cdc42Q61L, Rab2, Rab7, H-Ras and H-RasG12V) and single-plex formats (Rac1, Rac1Q61L and GST-GFP). GTPases and the GST-GFP control were individually bound to glutathione beads overnight at 4° C., washed with HPSE buffer, then resuspended together or assayed individually in the same buffer containing DTT and BSA. Bound GTPases were analyzed by mixing 5 µl protein-bound beads with 2.5-100 nM BODIPY-GTP in a total volume of 10 µl and incubating with rotation at 4° C. for 90 min. DMSO controls and samples treated with 10 µM of each test compound were run in parallel. Bound fluorescent nucleotide was measured using a Cyan ADP flow cytometer. Data were converted to ASCII format using IDLeQuery, exported and analyzed using Prism (GraphPad Software, Inc., San Diego, Calif.) non-linear, one-site binding.

GTPase activators were identified on the basis of an increase in fluorescent GTP-binding. In dose response assays, the following seven criteria were used to identify active compounds: (1)-8<LOGEC50<-4 (the computed EC50 value should be in the interval of tested concentrations); (2) 0.5<|HILLSLOPE|<2 (the absolute value of HILLSLOPE should be higher than 0.5 and lower than 2); (3) [TOP−STD_TOP]>[BOTTOM+STD_BOTTOM] (the amplitude of the biological signal should be statistically significant); (4) |LOGEC50|>STD_LOGEC50 (the standard error of LOGEC50 should be lower than the absolute value of LOGEC50); (5)|HILLSLOPE|>STD_HILLSLOPE (idem for the HILLSLOPE); (6) [TOP−BOTTOM] scavenger<0.1*[TOP−BOTTOM] target (the inherent fluorescence of the test compound should be lower than 10% of the biological signal); (7) [TOP−BOTTOM]/TOP for GST-GFP<0.1*[TOP−BOTTOM]/TOP for the target (the interference of the compound with the GST/GSH interaction should be lower than 10% of the biological signal).

In experiments including magnesium, six GST-GTPases were assayed simultaneously in a single multiplex (Rac1 wt, Rac1Q61L, RhoA wt, RhoAL63, Cdc42 wt and Cdc42Q61L) and 1 nM BODIPY-FL-GTP binding was measured in the presence or absence of the serial drug dilution series. Each dose response series was run in duplicate.

Equilibrium Binding Assay

Wild-type GST-Cdc42 (4 µM) was bound to GSH-beads overnight at 4° C. Cdc42 on GSH-beads was depleted of nucleotide by incubating with 10 mM EDTA containing buffer for 20 min at 30° C., washing twice with NP-HPS buffer, then re-suspended in the same buffer containing 1 mM EDTA/or 1 mM $MgCl_2$, 1 mM DTT and 0.1% BSA. Cdc42 unbound sites were blocked by incubation of protein—bead complex for 15 min at RT. 30 µl of this suspension incubated with 20 mM inhibitor for 3 min at RT and added 30 µl of various concentrations of ice cold BODIPY-FL-GTP. Samples incubated at 4° C. for 45 min and binding of fluorescent nucleotide to enzyme measured using an Accuri flow cytometer. Raw data were exported and plotted using GraphPad Prism software.

Live Cell Microscopy

Live cell microscopy was carried out on RBL-2H3 cells. Cells were grown on coverslips overnight, washed and overlaid with Tyrode's buffer (10 mM Hepes, pH 7.4, 130 mM NaCl, 5 mM KCl, 1.4 mM $CaCl_2$, 1 mM $MgCl_2$, 5.6 mM glucose and 0.1% BSA). Time lapse images were taken after addition of 10 µM MLS000693334 (final concentration) at 60 s intervals for up to 30 min. Activation with Thy-1 cross-linking was performed as described {Surviladze, 1998 #50}. Briefly, RBL cells incubated with OX7 mAb (Santa Cruz Biotechnology) final concentration 50 ug/ml for 1 h at 37 C. The unbound OX7 mAb was washed out with Tyrode's solution and activation initiated by adding anti-mouse IgG (25 ug/ml) (Jackson Immunoresearch Laboratories). Imaging was performed using a Bio-Rad Radiance 2100 confocal microscope equipped with a 60×1.4 NA oil immersion objective equipped with Lasersharp3000 software.

Immunofluorescence Staining and Microscopy

Swiss 3T3 cells were grown on coverslips in DMEM plus 10% fetal calf serum (FCS; Gibco) at 37 C in 5% $CO_2$.

Subconfluent cells were starved overnight in DMEM without serum and incubated with 1 or 10 µM inhibitor for 1 h. As a positive control, cells were stimulated with 100 ng/ml bradykinin for 30 min, or 100 ng/ml EGF as previously described {Kozma, 1995 #24}. Cells were washed with phosphate buffered saline, fixed with 3% paraformaldehyde, permeabilized for 5 min with 0.1% Triton X-100 in Tyrode's buffer, blocked for 1 h with 1% BSA in Tyrode's buffer, and stained for 1 h with rhodamine-phalloidin or Cdc42 mAb (Cytoskeleton Inc., Denver, Colo.) for 1 h followed by Cy3-conjugated goat-anti-mouse antibody (Jackson Immunoresearch Laboratories) for 1 h, at RT.

RBL-2H3 cells were grown in RPMI supplemented with 10% fetal bovine serum on cover slips. Semi-confluent cells were washed with Tyrode's solution and incubated with DMSO (vehicle) or 10 µM MLS000693334 for 1 h at 37° C. Inhibitor treated and un-treated cells were stimulated with 1 µg/ml DNP-BSA for 30 min as previously described {Wilson, 1991 #52}. Activation stopped by transferring of samples on ice. Cells were washed with phosphate buffered saline and fixed with 3% paraformaldehyde followed by permeabilization for 5 min with 0.1% Triton X-100 in Tyrode's buffer. After blocking for 1 h with 1% BSA in Tyrode's buffer, cells were stained for 1 h with rhodamine-phalloidin (Cytoskeleton Inc.) and Cdc42 specific mAb (Cytoskeleton, Inc). FITC-conjugated anti-muse IgG was used as the secondary antibody. All incubations were performed at room temperature. For imaging, samples were mounted on glass slides using ProLong® Gold antifade reagent. A Zeiss LSM 510 microscope, 40× objective was used to collect images.

Preparation of Membrane Vesicles from Swiss 3T3 Cells

Membranes were prepared according to {Johnson, 2009}.

In Vitro Cdc42-GTPgS Formation Pull-down Analyses

For analysis of the effect of MLS000693334 on the formation of the GTP-bound form of Cdc42 in vitro, 40 nM His-Cdc42 wt incubated (20 min at 30 C) with various concentration of GTPγS in the presence of 1 mM EDTA containing NP-HPS buffer. Reaction stopped by adding of excess amount of $MgCl_2$. Mixture incubated with 15 µl PAK-PBD/beads (Cytoskeleton Inc., Denver, Colo.) for 1 h. Washed 2× and active Cdc42 analyzed by Western blot using mAb for Cdc42 (Cytoskeleton Inc., Denver, Colo.) and Mouse TrueBlot Ultra: Horseradish Peroxidase anti-mouse IgG (eBioscience. San Diego, Calif.) followed by ECL (Thermo Scientific, Rockford, Ill.).

Effect of MLS000693334 on Dbs Activity.

GSH-beads were coupled with Cdc42 wt, washed and incubated with 10 mM EDTA-NP-HPS for 20 min at 30° C. Nucleotide depleted enzyme washed with NP-HPS, and incubated with 2µCi [$^3$H]GDP in the presence of 1 mM EDTA (in NP-HPS buffer) for 20 min at 30° C. To prevent the dissociation of tritiated guanine nucleotide from the Cdc42, $MgCl_2$ was added to a final concentration 20 mM. [$^3$H]GDP-Cdc42-beads washed and re-suspended in GDP exchange buffer (NP-HPS with 1 mM EDTA, 5 mM $MgCl_2$, and 1 mM DTT) and 100 µl aliquots loaded in tubes and incubated with vehicle or 10 µM MLS000693334 for 15 min. Effect of the guanine nucleotide exchange factor domain, Dbs on GDP/GTP exchange in the presence and absence of inhibitor was measured after addition of 200 nM His-DBS (DH/PH domain). The GDP/GTP exchange reaction was initiated by addition of 250 nM GTP and incubation samples for 2 min 30 C. The reaction was stopped by transferring samples on ice. Cdc42-beads collected and washed twice with ice cold GDP exchange buffer and measured radioactivity, by loading samples in scintillation vial.

In Vitro Cdc42 Activation Assay Modified from ZS MS and Activator MS

For in vitro Cdc42 activation measurements, DMSO or an equal volume of SID57578341 in DMSO were incubated for 20 min at 30° C. with 40 nM His-Cdc42 protein and varying concentrations of GTPγS in 1 mM EDTA-containing buffer (NP-HPS). Further nucleotide exchange was inhibited with the addition of excess $MgCl_2$ (60 mM final) and transfer to ice. Activated Cdc42 protein was isolated from solution by adding 15 μl GST-PAK-PBD bound glutathione beads and rotation at 4° C. for 1 h. Activated Cdc42 bound to GST-PAK-PDB was resolved by SDS-PAGE (12% gels) and analyzed by immunoblot using mAb directed against Cdc42 (Cytoskeleton, Inc.) and ECL (Thermo Scientific, Rockford, Ill.). Quantification was by densitometry.

GLISA

Swiss 3T3 cells were continuously passaged at subconfluence and used to monitor the capacity of compounds to block stimulus-mediated activation of Cdc42, Rac1 or RhoA in vivo. Commercial GLISA kits customized to capture activated Cdc42, Rac1 or Rho from cell lysates were used per manufacturer's instructions (Cytoskeleton, Inc.). Cells were serum starved by sequentially removing serum over a three day period and treated with DMSO or 10 μM compound in DMSO for 20-30 min. Subsequently samples were treated with EGF (10 ng/ml for Rac1 and 100 ng/ml for Cdc42) for 2 min to activate Rac1 and Cdc42 or 5 U/ml calpeptin for 10 min to activate RhoA. DMSO treated cells were left unstimulated to determine baseline GTPase activation or stimulated without drug treatment to determine maximal GTPase activation. Cell lysates were snap frozen, active Cdc42 and Rac1 were quantified based on a PAK binding assay, active RhoA was quantified based on Rho GTP-binding protein interaction. All assays were performed in 96-well microtiter plates, Purified GTP-bound Cdc42, Rac1, or RhoA served as a standards to calculate ng active GTPase in the lysates.

Results

Primary Screening

For detection of GTP binding to small G-proteins we used bead-based multiplex flow cytometry assay {Surviladze, 2009}. This method, which allowed us to simultaneously measure activity of 6 different small GTPases in 10 ul sample, was used for HTS of 200,000 compounds in the MLSCN. Six individual GST-GTPases representative of Rho, Ras and Rab branches of the Ras-related GTPase family (Cdc42 wt, Rac1 wt, Rac1Q61L, Rab2 wt, Rab7 wt, and H-Ras wt) were first bound to GSH-beads of a particular fluorescence intensity. The individually conjugated beads were mixed, dispensed into 384-well plates and incubated with fluorescent GTP in the presence of each test compound. Protein-bound fluorescence served as the read-out and was measured using a HyperCyt flow cytometry system. After primary screening we identified 100-500 positive compounds for each target protein. The complete results from the multiplex screen are available on PubChem with PubChem Bioassay identification numbers of 761, 757, 764, 760, 758, and 759, respectively. The quality control Z' statistics were very good for each target. In particular, the average Z' was 0.87+/−0.04 for Cdc42, 0.85+/−0.04 for Rac1, and 0.90+/−0.03 for Rac1 activated mutant.

Analysis of the raw flow cytometric data, made with IDLeQuery software, and imported into an Excel template, revealed several general and specific inhibitors for small GTPases. Two compounds, were determined to be specific inhibitors for Cdc42 GTPases. These two compounds, MLS 000693334 and MLS 000862339 appear in FIG. 1.

Development of a SAR of Cdc42 GTPase Inhibitors

The identification of MLS00069334 and MLS00862339 as inhibitors of Cdc42 GTPase led the inventors to establish a structure activity relationship (SAR) with respect to compounds which are identified with Cdc42 GTPase inhibitor activity. It was determined through these efforts that the sulphonamide group was quite important for the activity of the compounds and derivatization of the other aryl groups on the dihydropyrazole pharmacore.

Modification of the N-phenyl-4-sulfonamide Moiety:

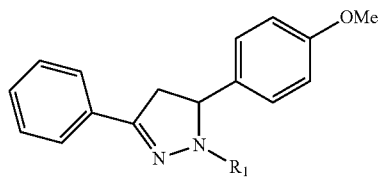

Bioisosteric replacement of the sulfonamide functional group produced compounds devoid of any significant inhibitory GTPase activity. Exchange of the phenylsulfonamide for a phenyl ring substituted in the 4-position with a sulphone (4-SO2CHF2), carboxylic acid (4-CO2H), amide (4-CO2NH2), or nitro (4-NO2) group resulted in complete loss of inhibitory activity. Removal of the sulfonamide or substitution with alkyl or alkoxy groups or halides, in combination with other changes on the structure, also dramatically attenuated the potency or efficacy (i.e., flat dose response curves) as compared to the hit compound. Migration of the sulfonamide group to alternate 2- or 3-positions on the phenyl ring produced analogs with inferior potency and efficacy profiles. As such, this key functionality was quickly assessed as a critical component of the scaffold that would be held constant as other structural features were surveyed.

Modification of the phenyl Moiety:

Modification of the parent scaffold resulted in 27 analogs. Substitutions made in concert with other structural alterations afforded an additional 27 analogs. Modifications focused on a survey of the electronic and spatial requirements for this region of the scaffold. The addition of substituents in any of the available positions on the phenyl ring generally produced analogs with decreased efficacy compared to the parent, thus generating very shallow and broad dose response curves. A few exceptions were found. Installation of a 2-methoxy group on the phenyl ring produced a compound with CID 44143702 (FIG. 10) which showed similar potency to the hit compound with Cdc42 ACT/WT activity of 5.5 μM

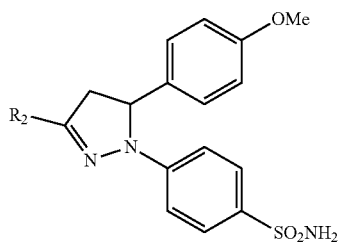

(42% efficacy) and 6.0 μM (59% efficacy), respectively. Replacement of the phenyl group with a 2-thiophene group gave compound with results similar, but not superior to, those observed with the parent hit (Table 5). The use of a 3-thiophene group resulted in a loss of potency and efficacy compared to the hit compound. Incorporation of alkyl groups in place of an aryl moiety was not beneficial.

TABLE 5

Selected examples of SAR from modifying the phenyl moiety (R2) of the MLS000693334 scaffold

| Entry | R2 | PubChem CID | Cdc42 ACT EC$_{50}$ μM | Cdc42 ACT Efficacy | Cdc42 WT EC$_{50}$ μM | Cdc42 WT Efficacy |
|---|---|---|---|---|---|---|
| 1 | 2-OMe-phenyl | 44143702 | 5.5 | 42% | 6 | 59% |
| 2 | 3-OMe-phenyl | 44143698 | 1.6 | 30% | 1.5 | 50% |
| 3 | 4-OMe-phenyl | 15201811 | 2.5 | 23% | 2.6 | 38% |
| 4 | 2-thiophene | 44143712 | 4 | 42% | 2.9 | 57% |
| 5 | 3-thiophene | 44143713 | 7.3 | 33% | 7.3 | 47% |
| 6 | methyl | 14870296 | >100 | 16% | >100 | 17% |
| 7 | tert-butyl | 44193701 | >100 | 29% | >100 | 33% |

Modification of the 4-methoxyphenyl moiety:

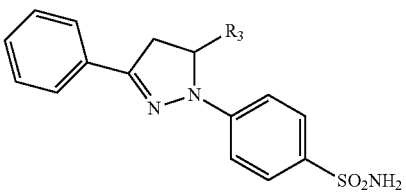

Systematic, single-point substitution of this particular phenyl ring (R$_3$) afforded 19 compounds with various electronically activating or deactivating groups. Changes made on this ring in combination with other structural modifications afforded an additional 39 analogs. Variations in this region yielded several compounds with a comparable or improved profile as compared to the parent hit in the primary dose response assay. Results of this effort are summarized in Table 6, below.

TABLE 6

Selected examples of SAR from modifying the 4-methoxyphenyl moiety

| Entry | R$_3$ | PubChem CID | Cdc42 ACT EC$_{50}$ μM | Cdc42 ACT Efficacy | Cdc42 WT EC$_{50}$ μM | Cdc42 WT Efficacy |
|---|---|---|---|---|---|---|
| 1 | phenyl | 2837695 | 16.8 | 44% | 31.6 | 56% |
| 2 | 2-Br-phenyl | 44216862 | >100 | NA | >100 | NA |
| 3 | 3-Br-phenyl | 44143703 | 3.7 | 50% | 3.3 | 55% |
| 4 | 4-Br-phenyl | 13927312 | 1.7 | 52% | 1.1 | 56% |
| 5 | 2-Cl-phenyl | 44193697 | 7.4 | 27% | 7.2 | 39% |
| 6 | 3-Cl-phenyl | 44193696 | 3.6 | 51% | 3.3 | 64% |
| 7 | 4-Cl-phenyl | 13927311 | 3.6 | 56% | 2.8 | 69% |
| 8 | 3-F-phenyl | 12005853 | 9.6 | 58% | 4.9 | 71% |
| 9 | 2-MeO-phenyl | 42628035 | 78.9 | 34% | 22.5 | 45% |
| 10 | 3-MeO-phenyl | 44143701 | 4.3 | 39% | 4.8 | 53% |
| 11 | 2-Me-phenyl | 44143704 | 13.6 | 42% | 16.6 | 55% |
| 12 | 3-Me-phenyl | 44143700 | 5.3 | 50% | 5.0 | 55% |
| 13 | 4-Me-phenyl | 13927310 | 5.0 | 46% | 5.0 | 66% |
| 14 | 3,4-diMeO-phenyl | 2971684 | 6.1 | 56% | 5.7 | 75% |

Substitutions at the 2-position of this phenyl ring resulted in deteriorated potency as compared to those same substitutions at the 3- or 4-position of the same ring (entries 2, 5, 9, and 11 in Table 6). Shaded entries represent analogs with sufficiently interesting potency and efficacy profiles that they were considered for secondary assay assessment.

Modification of the central dihydropyrazoline Core: This scaffold exists in a puckered conformation as a result of the dihydropyrazoline ring. Compounds possessing an aromatic pyrazoline ring with similar aromatic appendages have been the subject of clinical significance (Penning, 1997). In order to assess the effect of flattening out the scaffold in the context of GTPase activity, the analog featuring an oxidized central ring was prepared. The efficacy was sub-optimal, resulting in almost a flat dose response curve.

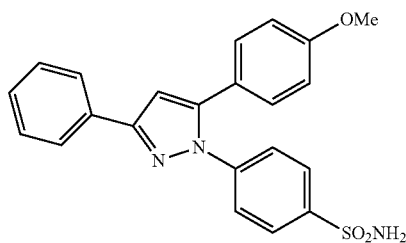

CID 14199398

Tandem Structural Modifications (Changes in More than One Region at a Time):

Many of the compounds in this category were screened as a part of a commercially available set and did not possess structural elements that we later discovered to be critical to effective inhibition of Cdc42. In most cases, these compounds lead to flat dose response curves or activation instead of the desired inhibitory activity. However, a few compounds were deliberately prepared as a means to incorporate structural features that were beneficial in previous SAR rounds as described above. One example was CID 44216842 (FIG. 9), featuring a combination of the best of what was learned from single point changes made during the course of SAR exploration. Knowing that a boost in potency was observed with these substituents, the 4-bromophenyl ($R_3$) and 3-methoxyphenyl ($R_2$) aryl groups were incorporated into the same analog. The result was a sub-micromolar potent, Cdc42 ACT/WT selective GTPase inhibitor, devoid of Rac activity. The efficacy of this analog was almost equivalent to that of the parent observed for Cdc42 ACT and ca. 10% less than that of the parent for Cdc42 WT.

Synthetic Chemistry (Following the General Scheme Set Forth in FIG. 8)

General experimental and analytical details: 1H and 13C NMR spectra were recorded on a Bruker AM 400 spectrometer (operating at 400 and 101 MHz respectively) in $CDCl_3$ with 0.03% TMS as an internal standard or DMSO-$d_6$. The chemical shifts (δ) reported are given in parts per million (ppm) and the coupling constants (J) are in Hertz (Hz). The spin multiplicities are reported as s=singlet, br. s=broad singlet, d=doublet, t=triplet, q=quartet, dd=doublet of doublet and m=multiplet. The LCMS analysis was performed on an Agilent 1200 RRL chromatograph with photodiode array UV detection and an Agilent 6224 TOF mass spectrometer. The chromatographic method utilized the following parameters: a Waters Acquity BEH C-18 2.1×50 mm, 1.7 μm column; UV detection wavelength=214 nm; flow rate=0.4 ml/min; gradient=5-100% acetonitrile over 3 minutes with a hold of 0.8 minutes at 100% acetonitrile; the aqueous mobile phase contained 0.15% ammonium hydroxide (v/v). The mass spectrometer utilized the following parameters: an Agilent multimode source which simultaneously acquires ESI+/APCI+; a reference mass solution consisting of purine and hexakis(1H, 1H, 3Htetrafluoropropoxy)phosphazine; and a make-up solvent of 90:10:0.1 MeOH:Water:Formic Acid which was introduced to the LC flow prior to the source to assist ionization. The melting point was determined on an Electrothermal MeI-Temp melting point apparatus.

Chalcone synthesis (Step 1): For analogs of MLS002699035, chalcones were synthesized as shown in step 1 of FIG. 10. The general procedure is described as follows: To a stirred solution of NaOH (1.2 eq, 6.25 mmol, 0.25 g) in $H_2O$ (2.5 mL) was added the ketone (1 eq, 5.0 mmol) in EtOH (1.5 mL). The solution was cooled to 0° C. and then the aldehyde (1 eq, 5.0 mmol) was gradually added. Once the addition was complete, the mixture was allowed to warm to room temperature and was stirred for 12-36 hours, until judged complete by LCMS. The reaction was quenched by the addition of $NH_4Cl$ sat. solution (4 mL) and extracted with EtOAc (2×8 mL). The organic layer was separated, combined, and dried over $Na_2SO_4$. Filtration and concentration of the solvent in vacuo afforded the desired product in sufficient purity for further use (Isleyen, 2007).

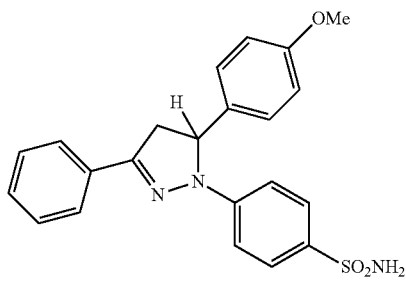 [SMILES: COc1ccc(C2CC(c3ccccc3)=NN2c2ccc(S(N)(=O)=O)cc2)cc1]

Probe: MLS002699035; CID: 2950007

4-[3-(4-methoxyphenyl)-5-phenyl-3,4-dihydropyrazol-2-yl]benzenesulfonamide: For the synthesis of this compound, the requisite chalcone starting material was commercially available. 4-Methoxychalcone (3, R1=H, R2=4-OMe, CAS#959-33-1) was purchased from Sigma-Aldrich and 4-hydrazinobenzene-1-sulfonamide hydrochloride (4, CAS#17852-52-7) was purchased from Acros Organics. (STEP 2): To a 20 mL microwave vial was added 4-methoxychalcone (0.238 g, 1.00 mmol, 1 eq), EtOH (200 proof, 10 mL), 4-hydrazinobenzene-1-sulfonamide hydrochloride (0.252 g, 1.13 mmol, 1.1 eq), and glacial AcOH (0.29 mL, 5.0 mmol, 5 eq). The vessel was sealed and then submitted to microwave irradiation at 150° C. for 1 h. Once the reaction mixture had cooled to room temperature, the cap was removed and the vessel was placed in a dry-ice/acetone bath. While stirring, hexane (10 mL) was added, and the resulting precipitate was collected by filtration. The precipitate was rinsed with hexane (3×10 mL) and then the solid was transferred to another flask and recrystallized from EtOH (6 mL). The solid was filtered, rinsed with hexanes (3×10 mL) and dried to afford 4-(5-(4-methoxyphenyl)-3-phenyl-4,5-dihydro-1Hpyrazol-1-yl)benzenesulfonamide (0.150 g, 37% yield, 97% purity) as white needles. $^1$H NMR (400 MHz, DMSO-$d_6$) δ 7.80 (m, 2H), 7.58 (d, J=9.0 Hz, 2H), 7.43 (m, 3H), 7.18 (d, J=8.7 Hz, 2H), 7.09 (d, J=9.0 Hz, 2H), 7.02 (s, 2H), 6.90 (d, J=8.7 Hz, 2H), 5.60 (dd, J=12.0, 5.1 Hz, 1H), 3.95 (dd, J=17.6, 12.0 Hz, 1H), 3.71 (s, 3H), 3.17 (dd, J=17.7, 5.1 Hz, 1H). $^{13}$C NMR (101 MHz, DMSO-d$_6$) δ 158.59, 149.58, 145.87, 133.48, 132.98, 131.83, 129.24, 128.69 (×2), 127.06 (×2), 126.99 (×2), 126.02 (×2), 114.42 (×2), 112.02 (×2), 61.88, 55.02, 42.97. Compounds of this chemotype submitted to LCMS analysis routinely showed a parent mass and/or a parent mass—2, the latter of which resulted presumably due to an analytical instrument artifact that resulted in oxidation/aromatization of the central dihydropyrazoline ring on the LCMS column, in the MS detector, or both. In this case, both ions were observed in the same peak. LCMS retention time: 3.057 min. HRMS m/z calculated for C22H21N3NaO3S [M++Na]: 430.1196. found 430.1180. For aromatized/oxidized signal, HRMS m/z calculated for C$_{22}$H$_{20}$N$_3$O$_3$S [M$^+$−2+1] 406.1225. found 406.1217. White needles, mp 185-187° C. (Faid-Allah, 1988).

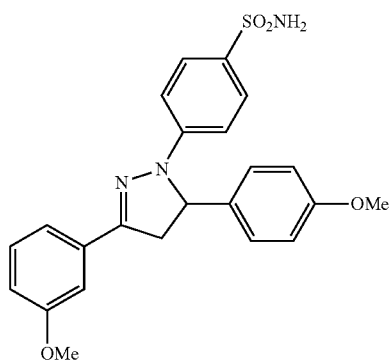 [SMILES: COc1ccc(C2CC(c3cccc(OC)c3)=NN2c2ccc(S(N)(=O)=O)cc2)cc1]

Analog: MLS002699036; CID: 44143698

4-[5-(3-methoxyphenyl)-3-(4-methoxyphenyl)-3,4-dihydropyrazol-2-yl]benzenesulfonamide: This analog was prepared as depicted in steps 1 and 2 in FIG. 8. Isolated 176 mg, 0.40 mmol, 96% yield, as a yellow solid. $^1$H NMR (400 MHz, DMSO-d$_6$) δ 7.58 (d, J=9.0 Hz, 2H), 7.36 (m, 2H), 7.32 (d, J=1.8 Hz, 1H), 7.17 (d, J=8.8 Hz, 2H), 7.09 (d, J=9.0 Hz, 2H), 7.02 (s, 2H), 6.98 (m, 1H), 6.90 (d, J=8.8 Hz, 2H), 5.59 (dd, J=12.0, 5.1 Hz, 1H), 3.92 (dd, J=17.7, 12.1 Hz, 1H), 3.82 (s, 3H), 3.70 (s, 3H), 3.17 (dd, J=17.7, 5.1 Hz, 1H). $^{13}$C NMR (101 MHz, DMSO-d$_6$) δ 159.45, 158.61, 149.52, 145.83, 133.49, 133.21, 133.03, 129.83, 127.07 (×2), 127.01 (×2), 118.59, 115.23, 114.44 (×2), 112.08 (×2), 110.96, 61.90, 55.21, 55.05, 43.04. LCMS retention time: 3.050 min. HRMS m/z calculated for C$_{23}$H$_{23}$N$_3$NaO$_4$S [M++Na]: 460.1301. found 460.1282. For aromatized/oxidized signal, HRMS m/z calculated for C$_{23}$H$_{22}$N$_3$O$_4$S [M$^+$−2+1] 436.1326. found 436.1319.

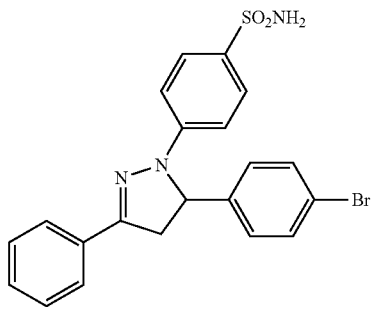 [SMILES: NS(=O)(=O)c1ccc(N2N=C(c3ccccc3)CC2c2ccc(Br)cc2)cc1]

Analog: MLS002699038; CID: 13927312

4-[3-(4-bromophenyl)-5-phenyl-3,4-dihydropyrazol-2-yl]benzene sulfonamide:

This analog was prepared as depicted in steps 1 and 2 in FIG. 10. Isolated 137 mg, 0.30 mmol, 71%) was observed as a white solid. $^1$H NMR (400 MHz, DMSO-d$_6$) δ 7.79 (dd, J=8.1, 1.5 Hz, 2H), 7.60 (d, J=9.0 Hz, 2H), 7.54 (d, J=8.5 Hz, 2H), 7.44 (m, 3H), 7.22 (d, J=8.5 Hz, 2H), 7.07 (d, J=9.0 Hz, 2H), 7.03 (s, 2H), 5.66 (dd, J=12.1, 5.0 Hz, 1H), 3.97 (dd, J=17.7, 12.1 Hz, 1H), 3.21 (dd, J=17.7, 5.1 Hz, 1H). $^{13}$C NMR (101 MHz, DMSO-d6) δ 149.72, 145.69, 140.97, 133.25, 132.00 (×2), 131.64, 129.38, 128.72 (×2), 128.12 (×2), 127.19 (×2), 126.11 (×2), 120.66, 112.02 (×2), 61.69, 42.69. LCMS retention time: 3.269 min. For aromatized/oxidized signal, HRMS m/z calculated for C$_{21}$H$_{17}$BrN$_3$O$_2$S [M$^+$−2+1] 454.0219. found 454.0221.

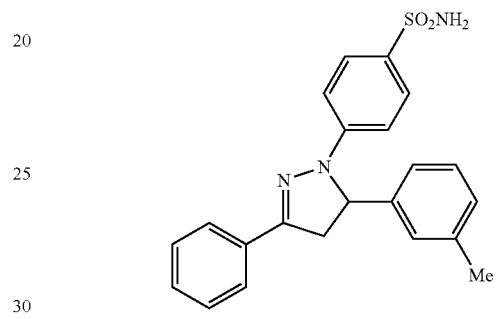

Analog: MLS002699039; CID: 44143700

4-[3-(3-methylphenyl)-5-phenyl-3,4-dihydropyrazol-2-yl]benzene sulfonamide:

This analog was prepared as depicted in steps 1 and 2 in FIG. 10. Isolated 90 mg, 0.23 mmol, 55% yield as a yellow solid. $^1$H NMR (400 MHz, DMSO-d6) δ 7.79 (dd, J=8.1, 1.5 Hz, 2H), 7.58 (d, J=9.0 Hz, 2H), 7.44 (m, 3H), 7.22 (t, J=7.6 Hz, 1H), 7.14-6.97 (m, 7H), 5.58 (dd, J=12.1, 5.4 Hz, 1H), 3.97 (dd, J=17.7, 12.2 Hz, 1H), 3.17 (dd, J=17.7, 5.4 Hz, 1H), 2.26 (s, 3H). $^{13}$C NMR (101 MHz, DMSO-d6) δ 149.59, 145.93, 141.75, 138.36, 133.04, 131.76, 129.29, 128.99, 128.72 (×2), 128.33, 127.13 (×2), 126.17, 126.07 (×2), 122.75, 111.93 (×2), 62.40, 43.04, 21.09. LCMS retention time: 3.212 min. For aromatized/oxidized signal, HRMS m/z calculated for C22H20N3O2S [M$^+$−2+1]: 390.1271. found 390.1268.

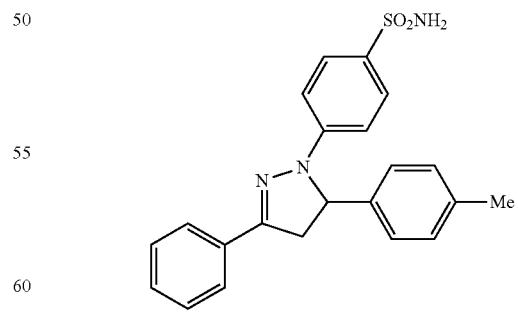

Analog: MLS002699040; CID: 13927310

4-[3-(4-methylphenyl)-5-phenyl-3,4-dihydropyrazol-2-yl]benzene sulfonamide

This analog was prepared as depicted in steps 1 and 2 in FIG. 10. Isolated 130 mg, 0.33 mmol, 79% yield as a yellow solid. ¹H NMR (400 MHz, DMSO-d6) δ 7.79 (dd, J=8.1, 1.5, 2H), 7.58 (d, J=9.0 Hz, 2H), 7.43 (m, 3H), 7.14 (s, 4H), 7.07 (d, J=8.9 Hz, 2H), 7.02 (s, 2H), 5.60 (dd, J=12.1, 5.1 Hz, 1H), 3.95 (dd, J=17.7, 12.1 Hz, 1H), 3.16 (dd, J=17.7, 5.1 Hz, 1H), 2.24 (s, 3H). ¹³C NMR (101 MHz, DMSO-d6) δ 149.60, 145.86, 138.64, 136.81, 132.99, 131.80, 129.63 (×2), 129.27, 128.71 (×2), 127.09 (×2), 126.04 (×2), 125.68 (×2), 112.00 (×2), 62.14, 42.94, 20.62. LCMS retention time: 3.224 min. For aromatized/oxidized signal, HRMS m/z calculated for C22H20N3O2S [M$^+$−2+1] 390.1271. found 390.1266.

Summary of Probe Properties: MLS002699035; CID: 2950007 (See Above)

Physical appearance and properties: The compound was isolated as white needles with melting point range of 185-187° C. The compound formed a mass when collected as described above that resembled spun wool.

LCMS behavior: Upon analysis by LCMS, compounds of this type commonly showed a mass consistent with aromatization/oxidation of the central dihydropyrazoline core, [M$^+$−2+1]. This was determined to be an artifact of the LCMS method, as the ratio of parent ion [M$^+$+1] to oxidized ion [M$^+$−2+1] could be modulated to a limited degree by varying the method parameters. Additionally, compounds that showed significant ratios of the two ions by LCMS were clearly pure by ¹H NMR and were not mixtures reflective of the observed LCMS product ratio.

It is also notable that intentionally prepared oxidized analogs were compared to their unoxidized dihydropyrazoline analogs by ¹H NMR and by bioassay. The oxidized compounds were easily recognized by diagnostic signals in the ¹H NMR and did not possess GTPase inhibitory activity.

¹H and ¹³C NMR in CDCl₃: The probe compound NMR characterization was obtained in DMSO-d₆ and CDCl₃. The DMSO data can be directly compared to the other analogs and is represented in the experimental section. The CDCl₃ data is offered here for convenience. ¹H NMR (400 MHz, CDCl₃) δ 7.73 (m, 2H), 7.67 (d, J=9.0 Hz, 2H), 7.39 (m, 3H), 7.15 (d, J=8.7 Hz, 2H), 7.07 (d, J=8.9 Hz, 2H), 6.84 (d, J=8.7 Hz, 2H), 5.31 (dd, J=12.1, 5.8 Hz, 1H), 4.60 (s, 2H), 3.85 (dd, J=17.3, 12.1 Hz, 1H), 3.76 (s, 3H), 3.18 (dd, J=17.3, 5.8 Hz, 1H). ¹³C NMR (101 MHz, CDCl₃) δ 159.55, 149.75, 147.59, 133.43, 132.24, 130.43, 129.66, 128.91 (×2), 128.25 (×2), 127.09 (×2), 126.33 (×2), 114.98 (×2), 112.82 (×2), 63.32, 55.53, 43.92.

Literature precedent of synthesis and melting point: The synthesis and melting point of this compound has been described (Faid-Allah, 1988). The literature melting point was reported as 216° C. which was higher than that which was experimentally determined in our lab (mp 185-187° C.). We cannot account for the discrepancy, but we noted it.

Tabulated Summary of Known Probe Properties:

Comparison to Prior Art for Cdc42 Inhibitors

There was no prior art describing direct Cdc42 inhibitors, so the discoveries reported here are highly innovative and impactful. Shown below is the structure of Secramine which is not a direct inhibitor of Cdc42. The compound was synthesized predicated on brefeldin A, which is a fungal metabolite that stabilizes a complex between Arf and Arf GEF thereby blocking GTPase activation (Pelish 2006),

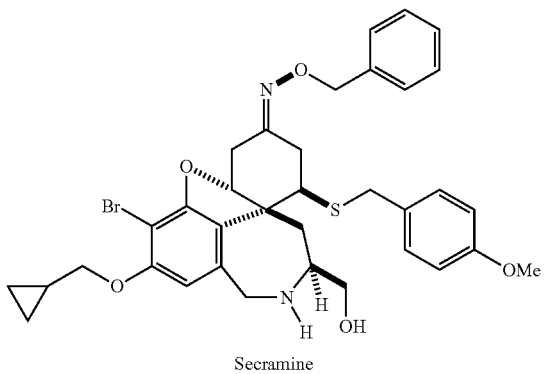

Secramine

Summary

The experimental studies described herein represent the first efforts to investigate the direct inhibition of Cdc42 GTPase as therapeutic targets. The compounds identified are dihydropyrazole compounds and show efficacy as inhibitors of Cdc42 GTPase for use in therapy where Cdc42 GTPase is implicated.

REFERENCES (FIRST SET)

1. Takai, Y., Sasaki, T. & Matozaki, T. Small GTP-binding proteins. Physiol. Rev. 81, 153-208 (2001).
2. Raftopoulou, M. & Hall, A. Cell migration: Rho GTPases lead the way. Dev. Biol. 265, 23-32 (2004).
3. Wennerberg, K., Rossman, K. L. & Der, C. J. The Ras superfamily at a glance. J. Cell Sci. 118, 843-846 (2005).
4. Stein, M. P., Dong, J. & Wandinger-Ness, A. Rab proteins and endocytic trafficking:potential targets for therapeutic intervention. Adv. Drug Deliv. Rev. 55, 1421-1437 (2003).
5. Brumell, J. H. & Scidmore, M. A. Manipulation of rab GTPase function by intracellularbacterial pathogens. Microbiol. Mol. Biol. Rev. 71, 636-652 (2007).
6. Minutolo, F. et al. Variously substituted (phosphonoacetamido)oxy analogues of geranylgeranyl diphosphate (GGdP) as GGdP-transferase (GGTase) inhibitors and antiproliferative agents. Med. Chem. 1, 239-244 (2005).
7. Morgillo, F. & Lee, H. Y. Lonafarnib in cancer therapy. Expert Opin. Investig. Drugs 15, 709-719 (2006).
8. Druker, B. J. et al. Effects of a selective inhibitor of the Abl tyrosine kinase on the growth of Bcr-Abl positive cells. Nat. Med. 2, 561-566 (1996).
9. Traxler, P. et al. Use of a pharmacophore model for the design of EGF-R tyrosine kinase inhibitors: 4-(phenylamino)pyrazolo[3,4-d]pyrimidines. J. Med. Chem. 40, 3601-3616 (1997).
10. Ciardiello, F. et al. Antitumor effect and potentiation of cytotoxic drugs activity in human cancer cells by ZD-1839 (Iressa), an epidermal growth factor receptor-selective tyrosine kinase inhibitor. Clin. Cancer Res. 6, 2053-2063 (2000).
11. Al-Obeidi, F. A. & Lam, K. S. Development of inhibitors for protein tyrosine kinases. Oncogene 19, 5690-5701 (2000).
12. Buday, L. & Downward, J. Many faces of Ras activation. Biochim. Biophys. Acta (2008).
13. Jaffe, A. B. & Hall, A. Rho GTPases: biochemistry and biology. Annu. Rev. Cell Dev. Biol. 21, 247-269 (2005).
14. Bucci, C. & Chiariello, M. Signal transduction gRABs attention. Cell Signal. 18, 1-8 (2006).

15. Brown, R., Marshall, C. J., Pennie, S. G. & Hall, A. Mechanism of activation of an N-ras gene in the human fibrosarcoma cell line HT1080. EMBO J. 3, 1321-1326 (1984).
16. Bar-Sagi, D. & Feramisco, J. R. Microinjection of the ras oncogene protein into PC 12 cells induces morphological differentiation. Cell 42, 841-848 (1985).
17. Braun, B. S. & Shannon, K. Targeting Ras in myeloid leukemias. Clin. Cancer Res. 14, 2249-2252 (2008).
18. Schwartz, S. L., Cao, C., Pylypenko, O., Rak, A. & Wandinger-Ness, A. Rab GTPases at a glance. J. Cell Sci. 120, 3905-3910 (2007).
19. Cheng, K. W., Lahad, J. P., Gray, J. W. & Mills, G. B. Emerging role of RAB GTPases in cancer and human disease. Cancer Res 65, 2516-2519 (2005).
20. Williams, D. A. et al. Dominant negative mutation of the hematopoietic-specific Rho GTPase, Rac2, is associated with a human phagocyte immunodeficiency. Blood 96, 1646-1654 (2000).
21. Aspenstrom, P., Lindberg, U. & Hall, A. Two GTPases, Cdc42 and Rac, bind directly to a protein implicated in the immunodeficiency disorder Wiskott-Aldrich syndrome. Curr. Biol. 6, 70-75 (1996).
22. Khosravi-Far, R. et al. Dbl and Vav mediate transformation via mitogen-activated protein kinase pathways that are distinct from those activated by oncogenic Ras. Mol. Cell. Biol. 14, 6848-6857 (1994).
23. Habets, G. G. et al. Identification of an invasion-inducing gene, Tiam-1, that encodes a protein with homology to GDP-GTP exchangers for Rho-like proteins. Cell 77, 537-549 (1994).
24. Patel, V. et al. Persistent activation of Rac1 in squamous carcinomas of the head and neck: evidence for an EGFR/Vav2 signaling axis involved in cell invasion. Carcinogenesis 28, 1145-1152 (2007).
25. Ellenbroek, S. I. & Collard, J. G. Rho GTPases: functions and association with cancer. Clin. Exp. Metastasis 24, 657-672 (2007).
26. Gao, Y., Dickerson, J. B., Guo, F., Zheng, J. & Zheng, Y. Rational design and characterization of a Rac GTPase-specific small molecule inhibitor. Proc. Natl. Acad. Sci. USA 101, 7618-7623 (2004).
27. Nassar, N., Cancelas, J., Zheng, J., Williams, D. A. & Zheng, Y. Structure-function based design of small molecule inhibitors targeting Rho family GTPases. Curr. Top. Med. Chem. 6, 1109-1116 (2006).
28. Schwartz, S. L. et al. Flow cytometry for real-time measurement of guanine nucleotide binding and exchange by Ras-like GTPases. Anal. Biochem. 381, 258-266 (2008).
29. Nolan, J. P. & Sklar, L. A. The emergence of flow cytometry for sensitive, real-time measurements of molecular interactions. Nat. Biotechnol. 16, 633-638 (1998).
30. Kuckuck, F. W., Edwards, B. S. & Sklar, L. A. High throughput flow cytometry. Cytometry 44, 83-90 (2001).
31. Young, S. M. et al. High-throughput screening with HyperCyt flow cytometry to detect small molecule formylpeptide receptor ligands. J. Biomol. Screen 10, 374-382 (2005).
32. Sklar, L. A., Carter, M. B. & Edwards, B. S. Flow cytometry for drug discovery, receptor pharmacology and high-throughput screening. Curr. Opin. Pharmacol. 7, 527-534 (2007).
33. Simons, P. C. et al. Simultaneous in vitro Molecular Screening of Six Bcl-2 Family Protein—Peptide Interactions by Flow Cytometry. Nature Protocols In Press, (2008).
34. Bagrodia, S., Taylor, S. J., Creasy, C. L., Chernoff, J. & Cerione, R. A. Identification of a mouse p21Cdc42/Rac activated kinase. J. Biol. Chem. 270, 22731-22737 (1995).
35. Lim, L., Manser, E., Leung, T. & Hall, C. Regulation of phosphorylation pathways by p21 GTPases. The p21 Ras-related Rho subfamily and its role in phosphorylation signaling pathways. Eur. J. Biochem. 242, 171-185 (1996).
36. Thompson, G., Owen, D., Chalk, P. A. & Lowe, P. N. Delineation of the Cdc42/Rac-binding domain of p21-activated kinase. Biochemistry 37, 7885-7891 (1998).
37. Benard, V. & Bokoch, G. M. Assay of Cdc42, Rac, and Rho GTPase activation by affinity methods. Methods Enzymol. 345, 349-359 (2002).
38. Ridley, A. J., Paterson, H. F., Johnston, C. L., Diekmann, D. & Hall, A. The small GTPbinding protein rac regulates growth factor-induced membrane ruffling. Cell 70, 401-410 (1992).
39. Nobes, C. D. & Hall, A. Rho, rac, and cdc42 GTPases regulate the assembly of multimolecular focal complexes associated with actin stress fibers, lamellipodia, and filopodia. Cell 81, 53-62 (1995).
40. Guillemot, J. C., Montcourrier, P., Vivier, E., Davoust, J. & Chavrier, P. Selective control of membrane ruffling and actin plaque assembly by the Rho GTPases Rac1 and CDC42 in FcepsilonRI-activated rat basophilic leukemia (RBL-2H3) cells. J. Cell Sci. 110, 2215-2225 (1997).
41. Djouder, N., Prepens, U., Aktories, K. & Cavalie, A. Inhibition of calcium releaseactivated calcium current by Rac/Cdc42-inactivating clostridial cytotoxins in RBL cells. J. Biol. Chem. 275, 18732-18738 (2000).
42. Itoh, R. E. et al. Activation of rac and cdc42 video imaged by fluorescent resonance energy transfer-based single-molecule probes in the membrane of living cells. Mol. Cell Biol. 22, 6582-6591 (2002).
43. Shutes, A. et al. Specificity and mechanism of action of EHT 1864, a novel small molecule inhibitor of Rac family small GTPases. J. Biol. Chem. 282, 35666-35678 (2007).
44. Parsons, J. T. Integrin-mediated signalling: regulation by protein tyrosine kinases and small GTP-binding proteins. Curr. Opin. Cell Biol. 8, 146-152 (1996).
45. Chigaev, A., Waller, A., Amit, O. & Sklar, L. A. Galphas-coupled receptor signaling actively down-regulates alpha4beta1-integrin affinity: a possible mechanism for cell deadhesion. BMC Immunol. 9, 26 (2008).
46. Onesto, C., Shutes, A., Picard, V., Schweighoffer, F. & Der, C. J. Characterization of EHT 1864, a novel small molecule inhibitor of Rac family small GTPases. *Methods Enzymol.* 439, 111-129 (2008).
47. Gupta, S. et al. Molecular cloning of IBP, a SWAP-70 homologous GEF, which is highly expressed in the immune system. *Hum. Immunol.* 64, 389-401 (2003).
48. Price, M. O., Atkinson, S. J., Knaus, U. G. & Dinauer, M. C. Rac activation induces NADPH oxidase activity in transgenic COSphox cells, and the level of superoxide production is exchange factor-dependent. *J. Biol. Chem.* 277, 19220-19228 (2002).
49. Denicola, G. & Tuveson, D. A. VAV1: a new target in pancreatic cancer? *Cancer Biol. Ther.* 4, 509-511 (2005).

REFERENCES (SECOND SET)

1. Agarwal V, Hammerschmidt S. Cdc42 and the phosphatidylinositol 3-kinase-Akt pathway are essential for PspC- 1. mediated internalization of pneumococci by respiratory epithelial cells. J Biol Chem. 2009; 284:19427-36.
2. Boettner B, Van Aelst L. The role of Rho GTPases in disease development. Gene. 2002 20; 286(2):155-74
3. Bos J L, Rehmann H, Wittinghofer A. GEFs and GAPs: critical elements in the control of small G proteins. Cell. 2007; 129(5):865-77.
4. Chang Y W, Bean R R, Jakobi R. Targeting RhoA/Rho kinase and p21-activated kinase signaling to prevent cancer development and progression. Recent Pat Anticancer Drug Discov. 2009; 4:110-24.
5. Chimini G, Chavrier P. Function of Rho family proteins in actin dynamics during phagocytosis and engulfment. Nat Cell Biol. 2000; 2: E191-6.
6. Dutra J M, Bonilha V L, De Souza W, Carvalho T M. Role of small GTPases in *Trypanosoma cruzi* invasion in MDCK cell lines. Parasitol Res. 2005; 96:171-7.
7. Etienne-Manneville S, Hall A: Rho GTPases in cell biology. Nature 2002; 420:629-635 Faid-Allah, H M; Mokhtar, H M. Pyrazole derivatives with possible hypoglycemic activity. Indian Journal of Chemistry, Section B: Organic Chemistry Including Medicinal Chemistry 1988; 27B: 245-249.
8. Gao Y, Dickerson J B, Guo F, Zheng J, Zheng Y. Rational design and characterization of a Rac GTPasespecific small molecule inhibitor. Proc Natl Acad Sci 2004 May 18; 101(20):7618-23.
9. Gómez del Pulgar T, Benitah S A, Valerón P F, Espina C, Lacal J C. Rho GTPase expression in tumorigenesis: evidence for a significant link. Bioessays. 2005; 27:602-13.
10. He B, Chen P, Chen S Y, Vancura K L, Michaelis S, Powers S. RAM2, an essential gene of yeast, and RAM1 encode the two polypeptide components of the farnesyltransferase that prenylates a-factor and Ras proteins. Proc Natl Acad Sci USA. 1991, 88:11373-7.
11. Isleyen, A; Dogan, O. Application of ferrocenyl substituted aziridinylmethanols (PAM) as chiral ligands in enantioselective conjugate addition of diethylzinc to enones. Tetrahedron: Asymmetry. 2007:18: 679-684.
12. Jaffe A B, Hall A: Rho GTPases: biochemistry and biology. Annu Rev Cell Dev Biol 2005; 21:247-269.
13. Johnson J L, Erickson J W, Cerione R A. New insights into how the Rho guanine nucleotide dissociation inhibitor regulates the interaction of Cdc42 with membranes. J. Biol. Chem. 2009; 284:23860-71.
14. Kozma R, Ahmed S, Best A, Lim L. The Ras-related protein Cdc42Hs and bradykinin promote formation of peripheral actin microspikes and filopodia in Swiss 3T3 fibroblasts. Mol Cell Biol. 1995; 15:1942-52.
15. Kuckuck F W, Edwards B S, Sklar L A. High throughput flow cytometry. Cytometry. 2001; 44:83-90.
16. Pelish H E, Peterson J R, Salvarezza S B, Rodriguez-Boulan E, Chen J L, Stamnes M, Macia E, Feng Y, Shair M D, Kirchhausen T. Secramine inhibits Cdc42-dependent functions in cells and Cdc42 activation in vitro. Nat Chem Biol. 2006; 2:39-46.
17. Penning, T D; Talley, J J; Bertenshaw, S R; Carter, J S; Collins, P W; Docter, S; Graneto, M J; Lee, L F; Malecha, J W; Miyashiro, J M; Rogers, R S; Rogier, D J; Yu, S S; Anderson, G D; Burton, E G.; Cogburn, J N; Gregory, S A; Koboldt, C M; Perkins, W E; Seibert, K; Veenhuizen, A W; Zhang, Y Y; Isakson, P C. Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib). J. Med. Chem. 1997:40: 1347-1365
18. Raftopoulou M, Hall A. Cell migration: Rho GTPases lead the way. Dev Biol. 2004; 265:23-32
19. Ridley A J. Rho GTPases and actin dynamics in membrane protrusions and vesicle trafficking. Trends Cell Biol. 2006
20. Rossman K L, Der C J, Sondek J. GEF means go: turning on RHO GTPases with guanine nucleotideexchange factors. Nat Rev Mol Cell Biol. 2005; 6:167-80
21. Sahai E, Marshall C J. RHO-GTPases and cancer. Nat Rev Cancer. 2002; 2:133-42.
22. Schwartz S L, Tessema M, Buranda T, Pylypenko O, Rak A, Simons P C, Surviladze Z, Sklar L A, Wandinger-Ness A. Flow cytometry for real-time measurement of guanine nucleotide binding and exchange by Ras-like GTPases. Anal Biochem. 2008; 381:258-66.
23. Shutes A, Onesto C, Picard V, Leblond B, Schweighoffer F, Der CJ. Specificity and mechanism of action of EHT1864, a novel small molecule inhibitor of Rac family small GTPases. J. Biol. Chem. 2007; 282:35666-78.
24. Surviladze Z, Dráberová L, Kubínová L, Dráber P. Functional heterogeneity of Thy-1 membrane microdomains in rat basophilic leukemia cells. Eur J Immunol. 1998; 28: 1847-58.
25. Surviladze Z, Waller A, Wu Y, Romero E, Edwards B S, Wandinger-Ness A, Sklar L A. Identification of a small GTPase inhibitor using a high-throughput flow cytometry bead-based multiplex assay. J. Biomol. Screen. 2010; 15:10-20.
26. Takai Y, Sasaki T, Matozaki T. Small GTP-binding proteins. Physiol Rev. 2001; 81:153-208.
27. Van den Broeke C, Radu M, Chernoff J, Favoreel H W. An emerging role for p21-activated kinases (Paks) in viral infections. Trends Cell Biol. 2010 Jan. 11. [Epub ahead of print]
28. Van Hennik P B, Hordijk P L. Rho GTPases in hematopoietic cells. Antioxid Redox Signal. 2005; 7:1440-55.
29. Vega F M, Ridley A J. Rho GTPases in cancer cell biology. FEBS Lett. 2008; 582:2093-101
30. Wilson B S, Seagrave J, Oliver J M. Impaired secretion and increased insolubilization of IgE-receptor complexes in mycophenolic acid-treated (guanine nucleotide-depleted) RBL-2H3 mast cells. J Cell Physiol. 1991; 149: 403-7
31. Yang L, Wang L, Zheng Y. Gene targeting of Cdc42 and Cdc42GAP affirms the critical involvement of Cdc42 in filopodia induction, directed migration, and proliferation in primary mouse embryonic fibroblasts. Mol Biol Cell. 2006; 17:4675-85.
32. Zhang B, Zhang Y, Shacter E, Zheng Y. Mechanism of the guanine nucleotide exchange reaction of Ras GTPase—evidence for a GTP/GDP displacement model. Biochemistry. 2005; 44:2566-76.

The invention claimed is:

1. A method of therapeutically treating ovarian cancer which overexpresses Cdc42 GTPase in a human patient in need comprising administering to said patient an effective amount of at least one compound according to the chemical structure:

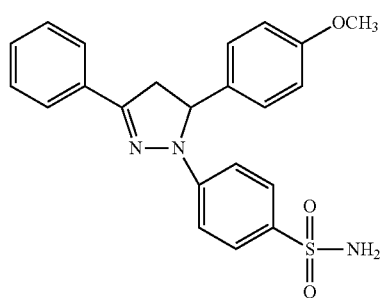
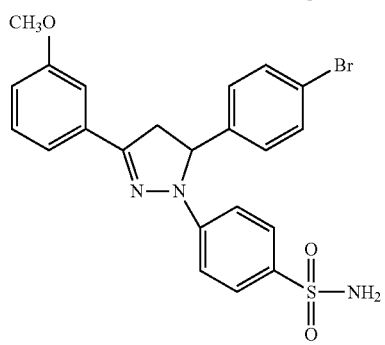
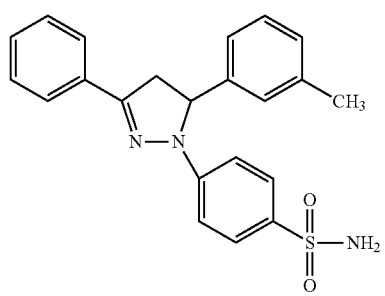
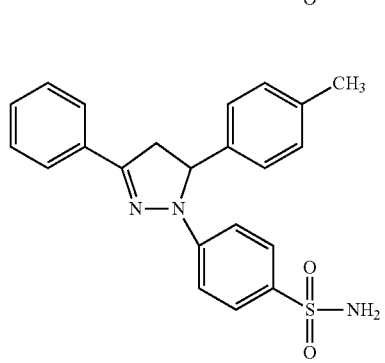
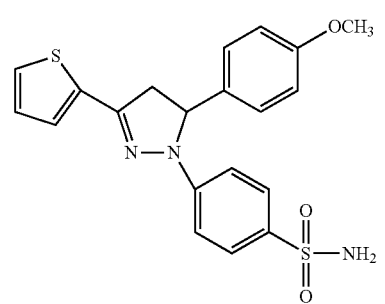
-continued
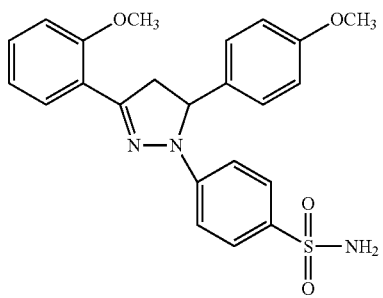
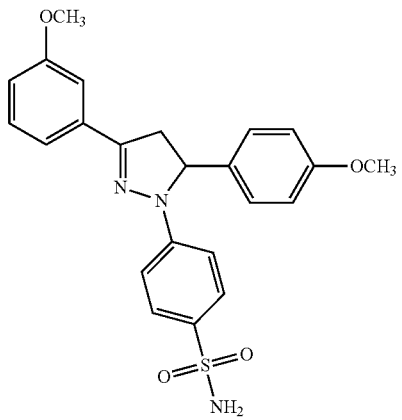
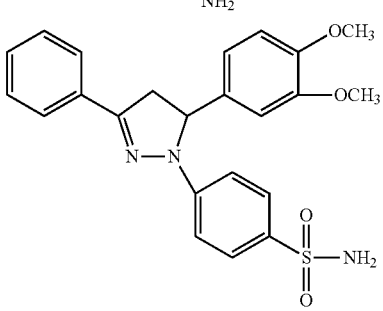
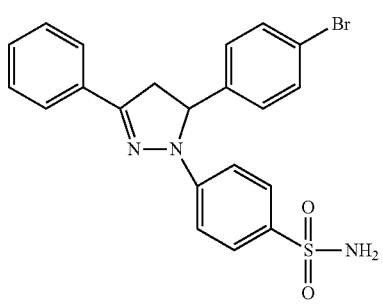 [SMILES: COc1ccc(C2CC(c3ccccc3)=NN2c2ccc(S(N)(=O)=O)cc2)cc1]
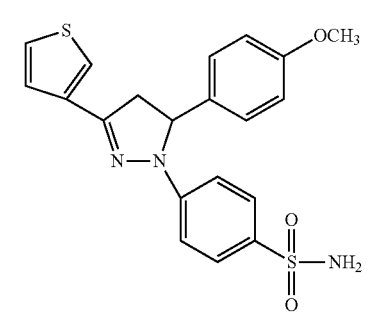

-continued

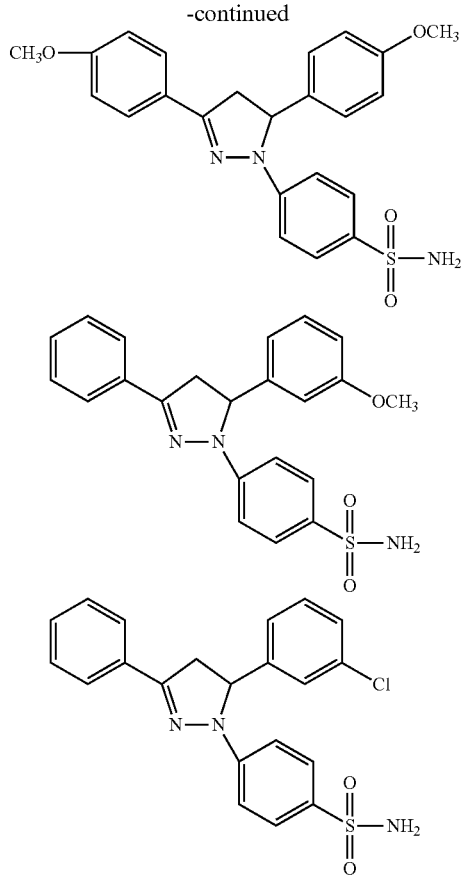

or a pharmaceutically acceptable salt and/or enantiomer thereof, optionally in combination with at least one additional anticancer agent.

2. The method according to claim 1 wherein said at least one compound is co-administered with at least one additional anticancer agent.

3. The method according to claim 1 wherein said compound is

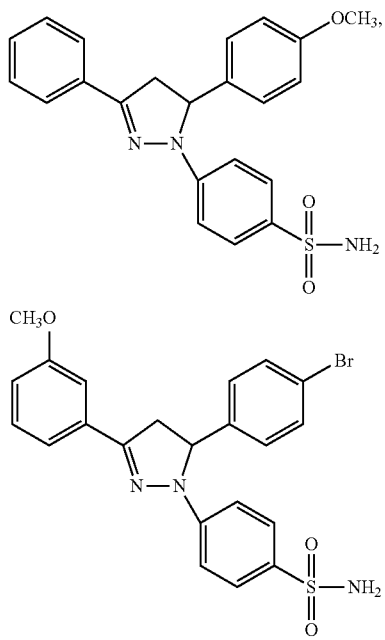

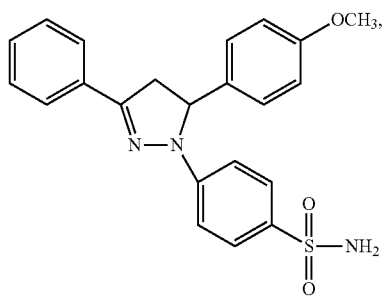

or a pharmaceutically acceptable salt and/enantiomer thereof.

4. The method according to claim 2 wherein said compound is

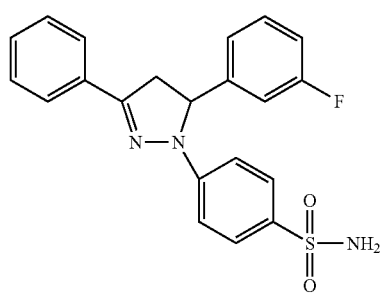

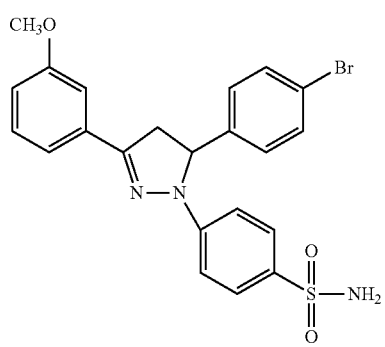

or a pharmaceutically acceptable salt and/enantiomer thereof.

5. The method according to claim 1 wherein said compound is

[Structure: 3-(3-methoxyphenyl)-5-(4-bromophenyl)-1-(4-sulfamoylphenyl)-4,5-dihydro-1H-pyrazole]

or a pharmaceutically acceptable salt and/or enantiomer thereof.

6. The method according to claim 2 wherein said compound is

[Structure: 3-(3-methoxyphenyl)-5-(4-bromophenyl)-1-(4-sulfamoylphenyl)-4,5-dihydro-1H-pyrazole]

or a pharmaceutically acceptable salt and/or enantiomer thereof.

7. The method according to claim 1 wherein said compound is

[Structure: 3-phenyl-5-(4-methoxyphenyl)-1-(4-sulfamoylphenyl)-4,5-dihydro-1H-pyrazole]

or a pharmaceutically acceptable salt and/or enantiomer thereof.

8. The method according to claim 2 wherein said compound is

[Structure: 3-phenyl-5-(4-methoxyphenyl)-1-(4-sulfamoylphenyl)-4,5-dihydro-1H-pyrazole]

or a pharmaceutically acceptable salt and/or enantiomer thereof.

9. The method according to claim 2 wherein said additional anticancer agent is selected from the group consisting of carboplatin, cisplastin, docetaxel, paclitaxel or a mixture thereof.

10. The method according to claim 6 wherein said additional anticancer agent is selected from the group consisting of carboplatin, cisplastin, docetaxel, paclitaxel or a mixture thereof.

11. The method according to claim 8 wherein said additional anticancer agent is selected from the group consisting of carboplatin, cisplatin, docetaxel, paclitaxel or a mixture thereof.

12. The method according to claim 1 wherein said cancer is metastatic.

13. The method according to claim 1 wherein said cancer is drug resistant.

14. The method according to claim 1 wherein said cancer is recurrent.

15. The method according to claim 2 wherein said cancer is metastatic.

16. The method according to claim 2 wherein said cancer is drug resistant.

17. The method according to claim 2 wherein said cancer is recurrent.

18. The method according to claim 5 wherein said cancer is metastatic.

19. The method according to claim 5 wherein said cancer is drug resistant.

20. The method according to claim 6 wherein said cancer is metastatic.

21. The method according to claim 6 wherein said cancer is drug resistant.

22. The method according to claim 8 wherein said cancer is metastatic.

23. The method according to claim 8 wherein said cancer is drug resistant.

24. The method according to claim 1 wherein said compound is administered to said patient in oral dosage form.

25. The method according to claim 1 wherein said compound is administered to said patient in parenteral dosage form.

26. The method according to claim 2 wherein said compound is administered to said patient in oral dosage form.

27. The method according to claim 2 wherein said compound is administered to said patient in parenteral dosage form.

28. The method according to claim 3 wherein said compound is administered to said patient in parenteral dosage form.

29. The method according to claim 5 wherein said compound is administered to said patient in parenteral dosage form.

30. The method according to claim 6 wherein said compound is administered to said patient in parenteral dosage form.

31. The method according to claim 7 wherein said compound is administered to said patient in parenteral dosage form.

32. The method according to claim 8 wherein said compound is administered to said patient in parenteral dosage form.

33. A method of reducing the likelihood that ovarian cancer which overexpresses Cdc42 GTPase in a human patient will metastasize, the method comprising administering to said patient an effective amount of at least one compound according to the chemical structure:

-continued

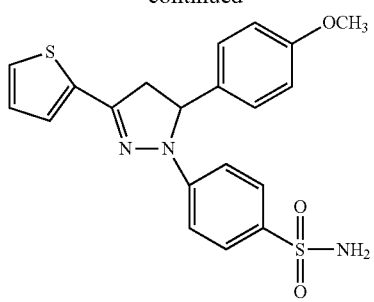

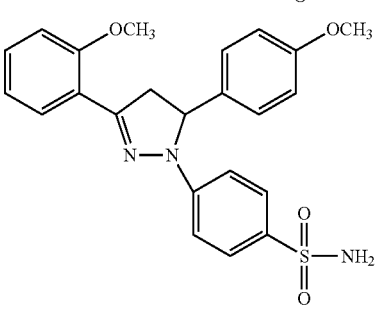

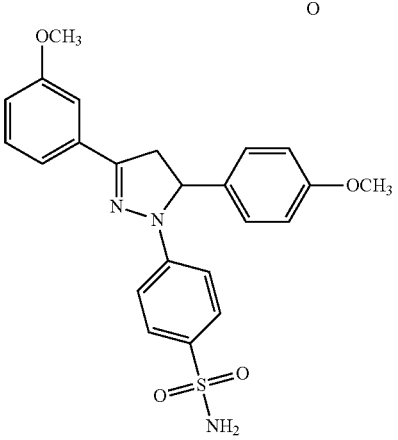

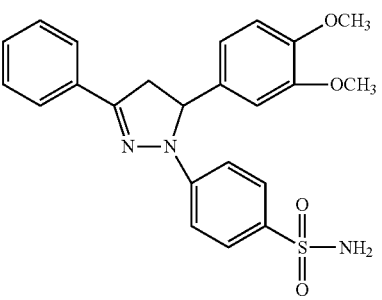

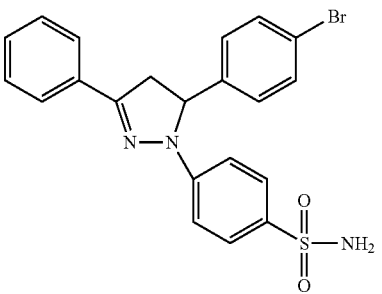 [SMILES: COc1ccc(C2CC(c3ccccc3)=NN2c2ccc(S(N)(=O)=O)cc2)cc1]

-continued

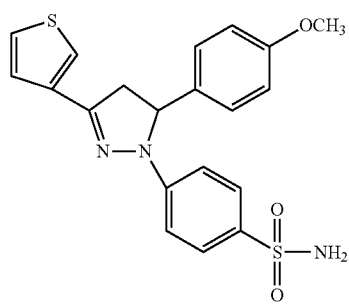

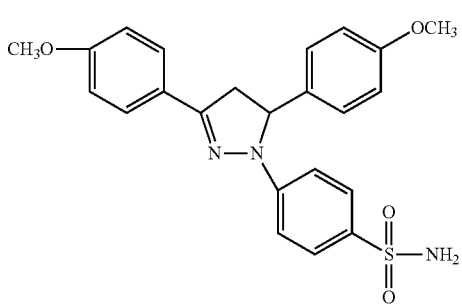

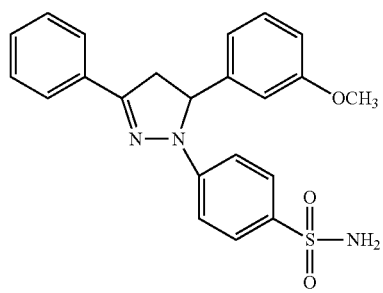

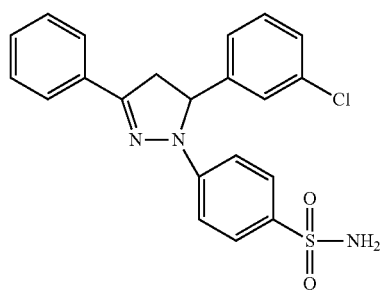

-continued

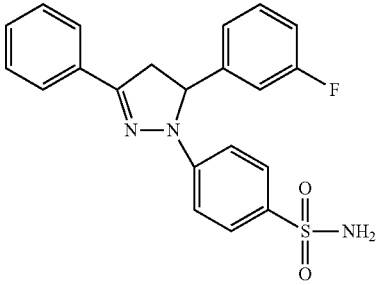

or a pharmaceutically acceptable salt and/or enantiomer thereof, optionally in combination with at least one additional anti-cancer agent.

34. The method according to claim 33 wherein said compound is

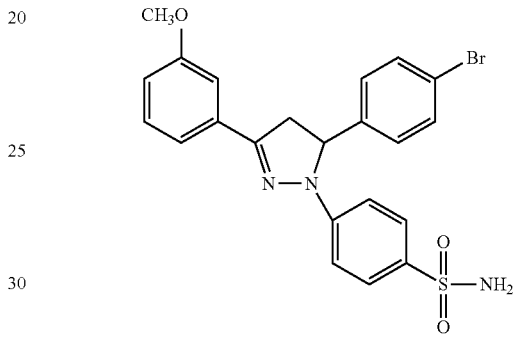

or a pharmaceutically acceptable salt and/or enantiomer thereof.

35. The method according to claim 33 wherein said compound is

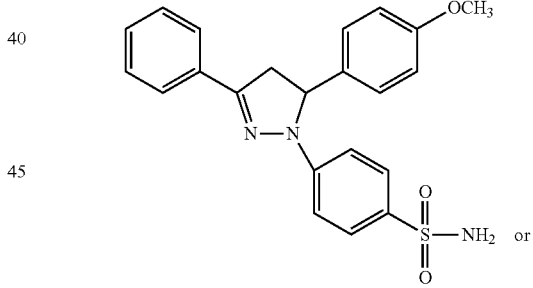

or

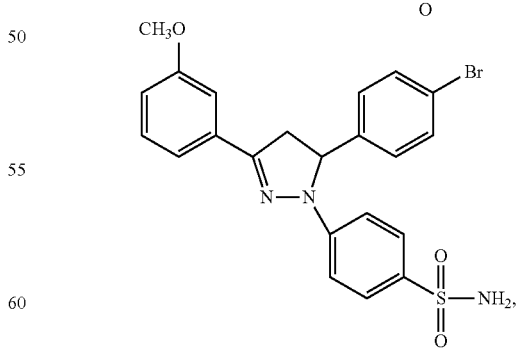

or a pharmaceutically acceptable salt and/or enantiomer thereof.

* * * * *